(12) United States Patent
Causevic et al.

(10) Patent No.: US 10,885,800 B2
(45) Date of Patent: Jan. 5, 2021

(54) HUMAN PERFORMANCE OPTIMIZATION AND TRAINING METHODS AND SYSTEMS

(71) Applicant: Skullcandy, Inc., Park City, UT (US)

(72) Inventors: Elvir Causevic, San Francisco, CA (US); Eldar Causevic, Wildwood, MO (US); Ines Kusturica, San Francisco, CA (US); Samuel R. Paschel, Jr., Park City, UT (US); S. Hoby Darling, Park City, UT (US); Emily Cook, Park City, UT (US); Samuel Noertiker, Oakley, UT (US); Kristopher C. Fike, Park City, UT (US); Thomas C. Burton, Midway, UT (US); Matthew Windt, Heber City, UT (US); Thomas Bishop, Park City, UT (US)

(73) Assignee: Skullcandy, Inc., Park City, UT (US)

( * ) Notice: Subject to any disclaimer, the term of this patent is extended or adjusted under 35 U.S.C. 154(b) by 360 days.

(21) Appl. No.: 14/988,244

(22) Filed: Jan. 5, 2016

(65) Prior Publication Data

US 2016/0196758 A1 Jul. 7, 2016

Related U.S. Application Data

(60) Provisional application No. 62/099,918, filed on Jan. 5, 2015.

(51) Int. Cl.
*G09B 5/00* (2006.01)
*A61B 5/16* (2006.01)
(Continued)

(52) U.S. Cl.
CPC ............... *G09B 5/00* (2013.01); *A61B 5/165* (2013.01); *A61B 5/486* (2013.01); *A61B 5/4836* (2013.01);
(Continued)

(58) Field of Classification Search
CPC ... G06F 19/3481; A61B 5/165; A61B 5/4836; A61B 5/486; A61B 5/47415; A61B 5/7415
(Continued)

(56) References Cited

U.S. PATENT DOCUMENTS 7,771,320 B2 8/2010 Riley et al.
2007/0087756 A1 4/2007 Hoffberg
(Continued)

FOREIGN PATENT DOCUMENTS

CN 101810923 A 8/2010
CN 102743252 A 10/2012

OTHER PUBLICATIONS

Ericsson et al., "The Role of Deliberate Practice in the Acquisition of Expert Performance", Psychological Review; 100(3):363-406 (1993).
(Continued)

*Primary Examiner* — James B Hull
(74) *Attorney, Agent, or Firm* — TraskBritt

(57) ABSTRACT

Presented are systems and methods that analyze an individual's state based on selected criteria, and then adaptively provide stimuli to affect the individual's performance compared to established benchmarks and pre-set plans. The methods or systems can provide audio and/or tactile inputs to a human subject to obtain a specific performance state. A music or sound selection engine considers the sensory and environmental inputs and selects the appropriate music or auditory stimulus, with the intent to reach a desired state of flow. The methods and systems can employ multiple measurements of personal data that can correlate to the emotional state of a subject. By manipulating stimuli delivered to an individual, ultimate performance can be improved over various planning horizons.

12 Claims, 12 Drawing Sheets

(51) Int. Cl.
 *A61B 5/00* (2006.01)
 *G06F 19/00* (2018.01)
 *A61B 5/0205* (2006.01)
(52) U.S. Cl.
 CPC ........ *A61B 5/7415* (2013.01); *G06F 19/3481* (2013.01); *A61B 5/02055* (2013.01); *A61B 5/4803* (2013.01); *A61B 2503/10* (2013.01); *A61B 2560/0242* (2013.01)
(58) Field of Classification Search
 USPC ....................................................... 434/236
 See application file for complete search history.

(56) References Cited

U.S. PATENT DOCUMENTS

| | | | | |
|---|---|---|---|---|
| 2007/0113725 | A1* | 5/2007 | Oliver | A61B 5/02438 84/612 |
| 2007/0270667 | A1* | 11/2007 | Coppi | A61B 5/222 600/300 |
| 2011/0105859 | A1* | 5/2011 | Popovic | A61B 5/02405 600/301 |
| 2011/0183305 | A1 | 7/2011 | Orbach | |
| 2012/0052476 | A1* | 3/2012 | Graesser | G09B 7/04 434/362 |
| 2012/0053928 | A1* | 3/2012 | Graesser | G09B 7/04 704/9 |
| 2012/0077160 | A1 | 3/2012 | DeGutis et al. | |
| 2012/0330869 | A1* | 12/2012 | Durham | G06N 5/022 706/16 |
| 2014/0357960 | A1 | 12/2014 | Phillips et al. | |
| 2016/0263439 | A1* | 9/2016 | Ackland | G06F 19/3481 |
| 2018/0278693 | A1* | 9/2018 | Binder | H04L 67/12 |
| 2019/0098090 | A1* | 3/2019 | Binder | H04L 67/12 |

OTHER PUBLICATIONS

Aubert et al., "Heart Rate Variability in Athletes", Sports Med 2003; 33(12):889-919 (2003).
Klauer et al., "The Impact of Driver Inattention on Near-Crash/Crash Risk: An Analysis Using the 100-Car Naturalistic Driving Study Data", U.S. Department of Transportation performed by Virginia Tech Transportation Institute, Technical Report—DOT HS 810 594; 226 pgs (Apr. 2006).
Park et al., "Nonlinear Discriminant Analysis Using Kernel Functions and the Generalized Singular Value Decomposition", Siam J. Matrix Anal. & Appl.; 27(1):87-102 (2006).
Dalton et al., "Effects of noise and music on human and task performance: A systematic reiview", Occupational Ergonomics; 7:143-152 (2007).
Orini et al., "A method for continuously assessing the autonomic response to music-induced emotions through HRV analysis", Med Biol Eng Comput; 48:423-433 (2010).
Bin Mansor et al., "Reckoning of Facial Grimacing Scheme for Patient Agitation in Critical Care", International Journal of Research and Reviews in Artificial Intelligence; 1(1):20-24 (2011).
Berry et al., "Educating the Educator: Use of Pulse Oximetry in Athletic Training", Athletic Training Education Journal; 7(2):74-80 (2012).
McConnell et al., "Auditory driving of the autonomic nervous system: Listening to theta-frequency binaural beats post-exercise increases parasympathetic activation and sympathetic withdrawal", Frontiers in Psychology; 5, Article 1248:10 pgs (2014).
International Patent Application No. PCT/US2016/012155, filed Jan. 5, 2016, by Skullcandy, Inc.: International Search Report and Written Opinion dated Mar. 28, 2016 (8 pgs).
Berger et al., "Removing Noise from Music Using Local Trigonometric Bases and Wavelet Packets", Journal of the Audio Engineering Society; 42(10):13 pgs (Oct. 1994).
Coles, "Cardiac and Respiratory Activity During Visual Search", Journal of Experimental Psychology; 96(2):371-379 (1972).
Devos, et al., "Towards a truly mobile auditory brain-computer interface: Exploring the P300 to take away", International Journal of Psychophysiology; 91(1):46-53 (2014).
Eberhardt, et al., "Automatic Feature Selection by Genetic Algorithms: Artificial Neural Nets and Genetic Algorithms", Proceedings of the International Conference in Prague, Czech Republic, published by Springer-Verlang Wien New York; 6 pgs (2001).
Epstein, "The Sports Gene: Inside the Science of Extraordinary Athletic Performance", published by the Penguin Group; p. 24 (2013).
Parncutt, et al., "The science and psychology of music performance: creative strategies for teaching and learning"; published by Oxford University, Music Education Research; 6(1):12 pgs (Mar. 2004).
Porges, et al., "Heart Rate Variability: An Index of Attentional Responsivity in Human Newborn", Developmental Psychology; 8(1):85-92 (1973).
Smith, "Deep Coaching: how to communicate more effectively with your athletes", Brian Mackenzie's Successful Coaching, ISSN 1745-7513: 5 pages (Jun. 2013). Also available from: http://www.brianmac.co.uk/articles/scni13a1.htm [Accessed Apr. 4, 2016].
Thong et al., "Correlating Heart Rate Variability with Skin Impedance Measurements", Proceedings of the 2005 IEEE, Engineering in Medicine and Biology 27th Annual Conference, Shanghai, China; 4 pgs (Sep. 2005).
Coifman, et al., "Selection of Best Bases for Classification and Regression", Proceedings on Information Theory and Statistics, 1994 IEEE-IMS Workshop; 5pgs (1994).
Burns et al., "Business Research Methods and Statistics using SPSS," Sage (2008).
Extended European Search Report for European Application No. 16735289.7 dated Jun. 4, 2018, 10 pages.
Chinese Search Report for Chinese Application No. 201680004984.8, dated Sep. 21, 2018, 1 page.
Chinese Office Action for Chinese Application No. 201680004984.8, dated Oct. 9, 2018, 9 pages.

* cited by examiner

HUMAN PERFORMANCE OPTIMIZATION AND TRAINING METHODS AND SYSTEMS

CROSS-REFERENCE TO RELATED APPLICATIONS

This application claims priority from U.S. Provisional Patent Application Ser. No. 62/099,918, filed Jan. 5, 2015, which is hereby incorporated herein by this reference in its entirety.

TECHNICAL FIELD

The present application relates to the science of human performance generally, and to methods and systems for optimizing human performance using feedback.

Several scientific literature articles are referenced throughout this specification, each of which is incorporated by reference in their entirety.

BACKGROUND

The fields of cognitive psychology and occupational ergonomics arose in the middle of the $20^{th}$ century as responses to an increasingly technological world. Cognitive psychology is the scientific study of the human mind and mental function, and attempts to answer questions regarding how learning takes place, how attention is maintained or lost, and the perception of data and information. Going further, cognitive psychology attempts to discover the pathways of reasoning, the operation and use of language, how conceptual development takes place in humans, and how decision making occurs. Cognition, in the modern psychological understanding of the term, models the human brain as a complex computing system in an effort to explain its many mysteries. Occupational ergonomics is the scientific study of the relationships between humans and their work environment, with an emphasis on performance optimization, as well as health and safety. One goal of occupational ergonomics is to ensure that the work or performance environment adequately comprehends and considers the anatomy, physiology, neurology, anthropometry, and biomechanics of the human.

Sports science is a recently established discipline that draws on the historical interest of medicine, physiology, psychology and biomechanics as they pertain to human performance in athletic contexts.

The concept of optimal experience, referred to alternatively as "flow" or "zone," is a frequent concern of sports science. The concept of flow was investigated by psychologist Mihaly Csikszentmihalyi and described as a pleasurable state of mind when a person's goals are clear, feedback is immediate and there is a balance between opportunity and capacity. In other words, the preconditions for flow are the human subject's focus on a goal that is nearly evenly matched to one's ability, where external variables such as conflict, distraction, contradiction, boredom and anxiety are absent, or nearly so.

The concept of flow has been described in diverse fields. Musicians and artists have described a state of effortless attention and relaxation, where the art is expressing itself through the artist without the artists' volition. Athletes describe getting into "the zone" where high performance is achieved without conscious effort, but as an unfolding of events. Video gamers experience being "at one" with the game they are playing, and computer programmers enter an altered state of unparalleled productivity where time seems to vanish. Martial artists relate the concept of flow to the egoless Zen state of "no-mindedness" where the mind is unattached to outcomes and therefore open to what is actually taking place in the moment without fear of what will follow. Others have defined it as a state where time does not exist—the passage of time is not noticeable, and the participant who enters the state of flow is not aware if minutes or hours passed while they were in it.

While attaining the flow state is described as highly psychologically pleasurable and the performance advantages recognized in many fields of endeavor, the occurrence of flow is mostly left to chance. Once experienced, the human subject is likely to replicate the circumstances that lead to the attainment of flow, but the actual cultivation of flow remains primarily an inward-looking or meditative discipline. Even with the highest levels of preparation and the clearest and most diligent goal-setting practices, entering a state of flow volitionally and consistently is an elusive goal outside of artificially controlled environments. State of flow to be induced in the athlete may be different depending on the training cycle, and may include both a drive to amplify level of activity, but also to attenuate it. This goal may depend be set instantaneously by the athlete, or set as a long-term training goal by the athlete or their coach.

In one study, professional pianists who performed a composition several times were studied when a flow state was attained. See Parncutt, R. et al., *The Science & Psychology of Music Performance: Creative Strategies for Teaching and Learning* Oxford University Press (2002), p. 119. In the flow state, the performer exhibited lowered heart rate and blood pressure, and relaxation of the facial muscles, conditions that correlate to relaxation. In athletics, studies involving heart rate variability have also been conducted to quantify elite performance attributes of the cardiovascular system, but understanding the interactions between the cardiovascular system and autonomic nervous system during physical exercise remains a difficult problem. See Aubert, A. et al., *Heart Rate Variability in Athletes*, Sports Med 2003:33(12).

In the famous paper *The Role of Deliberate Practice in the Acquisition of Expert Performance*, the authors posited that expertise in any endeavor required the accumulation of 10,000 hours of experience, a proposition that is now frequently cited as the "10,000 Hour Rule" or the "Deliberate Practice Framework," Psychological Review, Vol. 100 (3), July 1993, 363-406. Eriksen later explained that exceptional performance is possible for any healthy human once 10,000 hours of practice is accumulated, which has lead commentators to recognize that accumulating this level of practice often involves commitment, goal setting and focus and hours of time spent alone. See Epstein, D., *The Sports Gene: Inside the Science of Extraordinary Athletic Performance*, p. 24 (Penguin, 2013).

The role of the environment on concentration and human performance has been extensively studied, particularly by occupational ergonomics. While the role of noise as a distraction to cognition, learning and performance is well understood, the role of music is not understood. See Dalton, B. et al., *Effects of noise and music on human task performance: A systematic review*, Occupational Ergonomics 7 (2007) 143-152. Music can enhance cognition, learning and performance, or it can detract from it. In a complex task such as driving, the presence or absence of music has been shown to be one of the determining factors in performance. Id. at 145. During reading, music can be as distracting as noise, but in other studies, the presence of music has enhanced performance. Unfortunately, research in existing literature is incomplete and does not characterize conclusively which feature of music (tonality, melody, rhythm, tempo) affects performance positively or negatively. Id. at 147-149.

BRIEF SUMMARY

Exemplary embodiments employ multi-variate analyses of an individual's state based on selected criteria, and then adaptively provide stimuli to affect performance compared to established benchmarks and pre-set plans. In more specific exemplary embodiments, the methods or systems provide audio and/or tactile inputs to a human subject to obtain a specific performance state.

As depicted in FIG. 1A, an illustrative embodiment is shown in a block diagram 10. The user's context and performance 12 is gathered by various sensors and other data, sources, as described in greater detail below. A music or sound selection engine considers the sensory and environmental inputs and selects the appropriate music or auditory stimulus at 14, with the intent to reach desired state of flow at 16. For the purposes of this disclosure, "flow" is broadly intended to include mood states that correlate to achievement of a predefined performance level. The disclosure comprehends and describes multiple measurements of personal data that can correlate to emotional state or "mood." The illustrative system shown in FIG. 1A is shown as a loop, where the stimulus 14 is continuously correlated to updated user context and performance data 12. Ultimately, the state of flow is modulated over time to achieve the intended performance, athletic or otherwise.

FIG. 1B depicts another illustrative embodiment. The user's context and performance 22 includes personal user personal data 24 and environmental data 26 gathered by various sensors and other data sources, as described in greater detail below. As discussed in greater detail below, context and performance data 22 can include, but is not limited to, information such as GPS location, velocity data, velocity rate of change information, real-time and/or forecast meteorological data (e.g., wind speed, temperature, precipitation, alerts), accelerometer data, gyroscope data, compass data, ambient light level, body temperature, altimeter data, humidity, blood oxygenation, pulse rate, heart rate variability, eye movement, jaw tension, head orientation, posture data, microgrimace or facial gesture data, auditory evoked potential data, P300 response data, EEG data, acoustic data, speech pattern recognition data, impedance, capnographic data, ambient $O_2$ data, etc.

The collected data is fed in real- or near-real time to a stimulus selection engine at 28. A feature extraction routine selects the most important features to feed to use in selecting the stimulus, which can be audio or musical, or visual or tactile as discussed further below. The stimulus selection engine considers the sensory and environmental inputs, as well as short term and long term goals (such as training plans), and selects the appropriate music or auditory stimulus at 30, with the intent to reach desired state of flow. A music or auditory stimulus can be applied in the illustrative embodiment. The stimulus is delivered to the user at 32. When a flow state is indicated at 34, either by the user inputting a signal or by a predetermined combination of sensed conditions (as the system again performs a feature extraction routine from the sensed data to confirm that the user is in the correct flow state), it is compared to the desired flow state. If a desired flow state is not yet achieved, the system can loop back to the start. The stimulus can then be modified at 30 to modulate the correlative feature to either negatively or positively tune the flow state to conform to a performance plan as discussed in greater detail below. The illustrative system 20 shown in FIG. 1B is shown as a loop, where the modified stimulus is then correlated to updated user context and performance data 22. Ultimately, the state of flow is modulated over time to achieve the intended performance, athletic or otherwise.

The illustrative embodiment of FIG. 1C includes a performance plan 18, which can be implemented over a period of time, as discussed in greater detail below. The illustrative performance plan can be monitored and/or implemented with the assistance a coach 19 or other trusted party, as further discussed in detail below. A performance plan can be implemented over a period of hours, days, months or years. A coach can include more than one coach, and a coaching entity can provide performance training assistance to a plurality of processes 10.

Another aspect of an exemplary embodiment of the present invention employs statistical pattern-recognition techniques to derive classifiers of various user data into performance-based classes. Another aspect of an exemplary embodiment of the present invention uses feedback control loop theory to provide stimuli to a user in order to optimize user performance and achievement of membership in a desired performance-based class. Another aspect of an exemplary embodiment of the present invention uses audio stimuli to stimulate performance goals. Another aspect of an exemplary embodiment of the present invention is the use of nested control loops to achieve short-term and long-term performance goals in order to achieve a performance training goal over time. Another aspect of an exemplary embodiment of the present invention is the collection and pooling of data from model individuals in order to derive performance-based classes. Another aspect of an exemplary embodiment of the present invention is the collection and pooling of data from a large number of individuals that are subject to audio stimulus and processing that data to reveal statistically relevant human performance discriminant features for the construction of human performance-based classifiers.

A still further aspect of an exemplary embodiment of the present invention includes devices and systems for collecting performance-based data.

Yet another aspect of an exemplary embodiment of the present invention includes software applications for controlling data processing, data, acquisition and pattern recognition as well as implementing context-aware control loops using wearable devices, portable smartphone computation devices, portable and desktop computers, mainframe computers and network servers.

A further aspect of an exemplary embodiment of the present invention includes a method for the selection of a stimulus from among multiple stimuli based on human performance-based criteria.

According to an illustrative embodiment, a system and method for optimizing performance of an activity by a human subject is disclosed, the method performed by a system comprising at least one processor and at least one memory storing instructions which, when executed cause the system to perform the method, the method comprising acquiring data pertinent to the human subject; delivering the data to a stimulus selection engine; selecting a stimulus from among plural stimuli with the stimulus selection engine; outputting the selected stimulus to the human subject; determining a flow state value of the human subject.

The system or method employs context and performance data that includes at least one of GPS location, velocity data, velocity rate of change information, real-time and/or forecast meteorological data, accelerometer data, gyroscope data, compass data, ambient light level, body temperature, altimeter data, humidity, blood oxygenation, pulse rate, heart rate variability, eye movement, jaw tension, head orientation, posture data, microgrimace or facial gesture data, auditory evoked potential data, P300 response data, EEG data, acoustic data, speech pattern recognition data, impedance, capnographic data, or ambient $O_2$ data.

In another illustrative embodiment, a system is disclosed comprising: an environmental sensor module, a personal sensor module, a performance plan module, and an input module, said environmental sensor module, personal sensor module, performance plan module, and input module coupled to a data storage module coupled to a context module, a feature validation module, a user feedback control loop module, and a stimulus selection module and other modules; said data storage module for storing data and software instruction code used by said context module, feature validation module, user feedback control loop module, and stimulus selection module; an output module coupled to the data storage module; a resource module coupled to the data storage module; a context module that receives data from the data storage module and calculates a representation or model of the user's current state, including environmental and personal data.

The illustrative system can further include a feature validation module coupled to the data storage module; a subject feedback control loop module coupled to the context module; and a feature validation module; wherein the control loop module manages the delivery of stimuli to the user to increase or decrease current performance to attempt to closely match the parameters of the performance plan module.

The illustrative system can further include a subject feedback control loop module and a trusted party feedback module coupled to the user feedback control loop module, such that information related to the user's trajectory on a performance plan is transmitted to a trusted party.

The illustrative system can also have the user feedback control loop module coupled to a stimulus selection module, wherein the stimulus is an audio or music stimulus that is determined to alter user performance, as modeled by the user feedback control loop module, in order to bring current observed contextual performance into conformance with the output of the performance plan module.

In the illustrative system, the stimulus selection module can be configured to modify a stimulus based on the attenuation or amplification of features identified by the feature validation module.

DETAILED DESCRIPTION

Figure 1A:
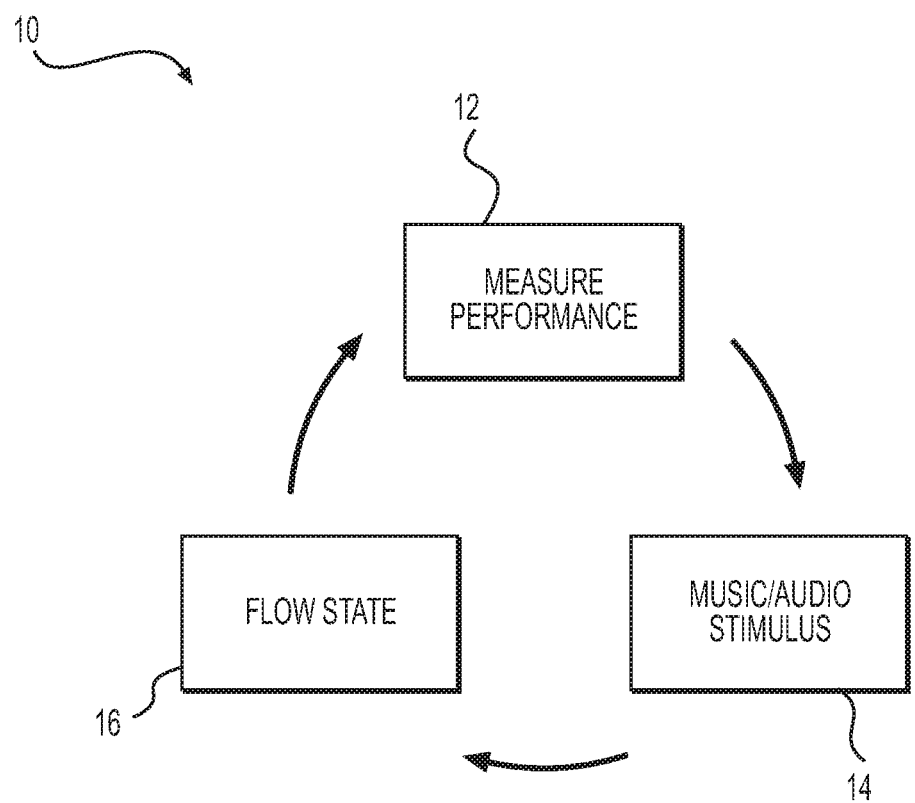
FIGS. 1A, 1B and 1C show exemplary system block diagrams.
Figure 1B:
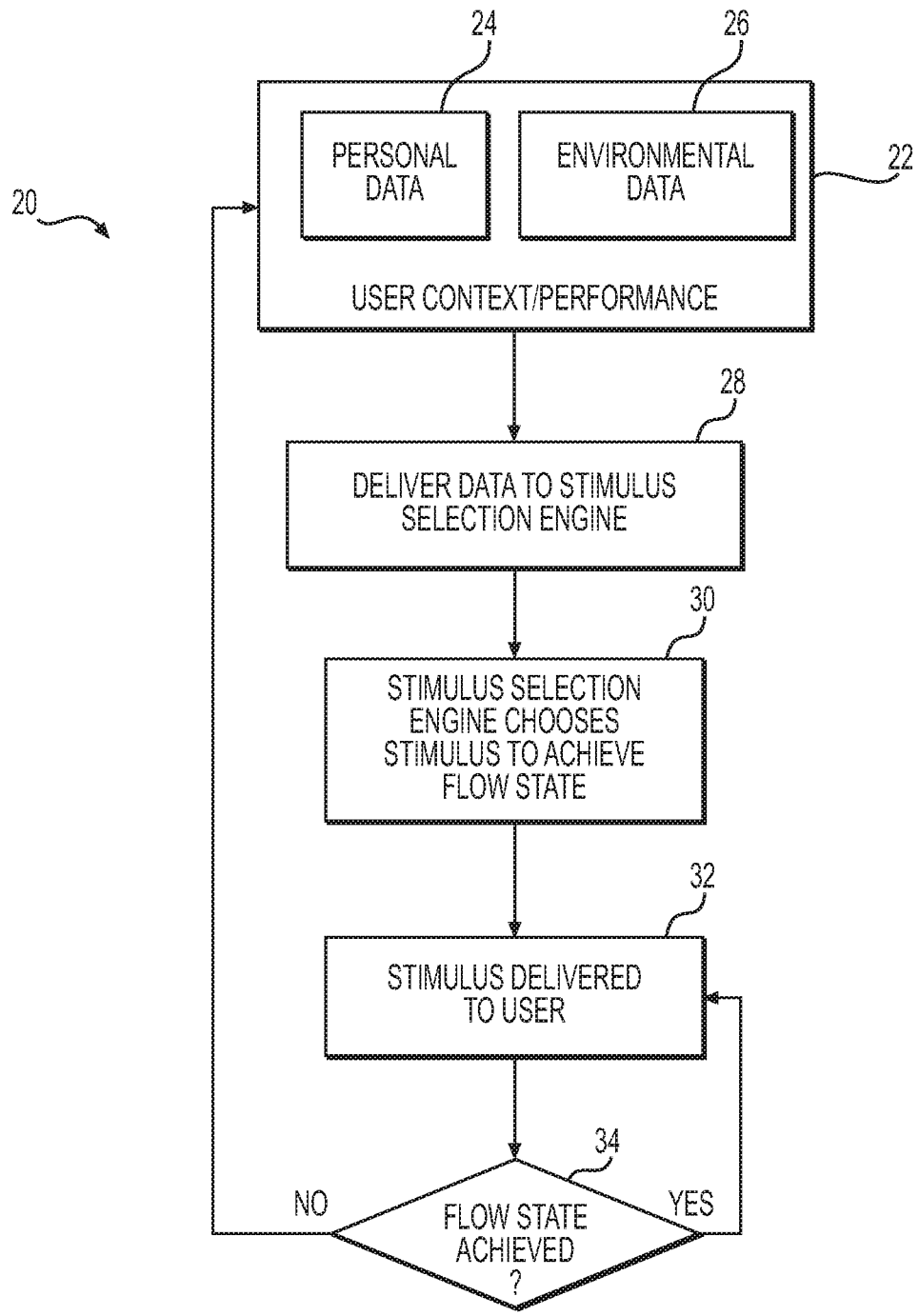
Figure 1C:
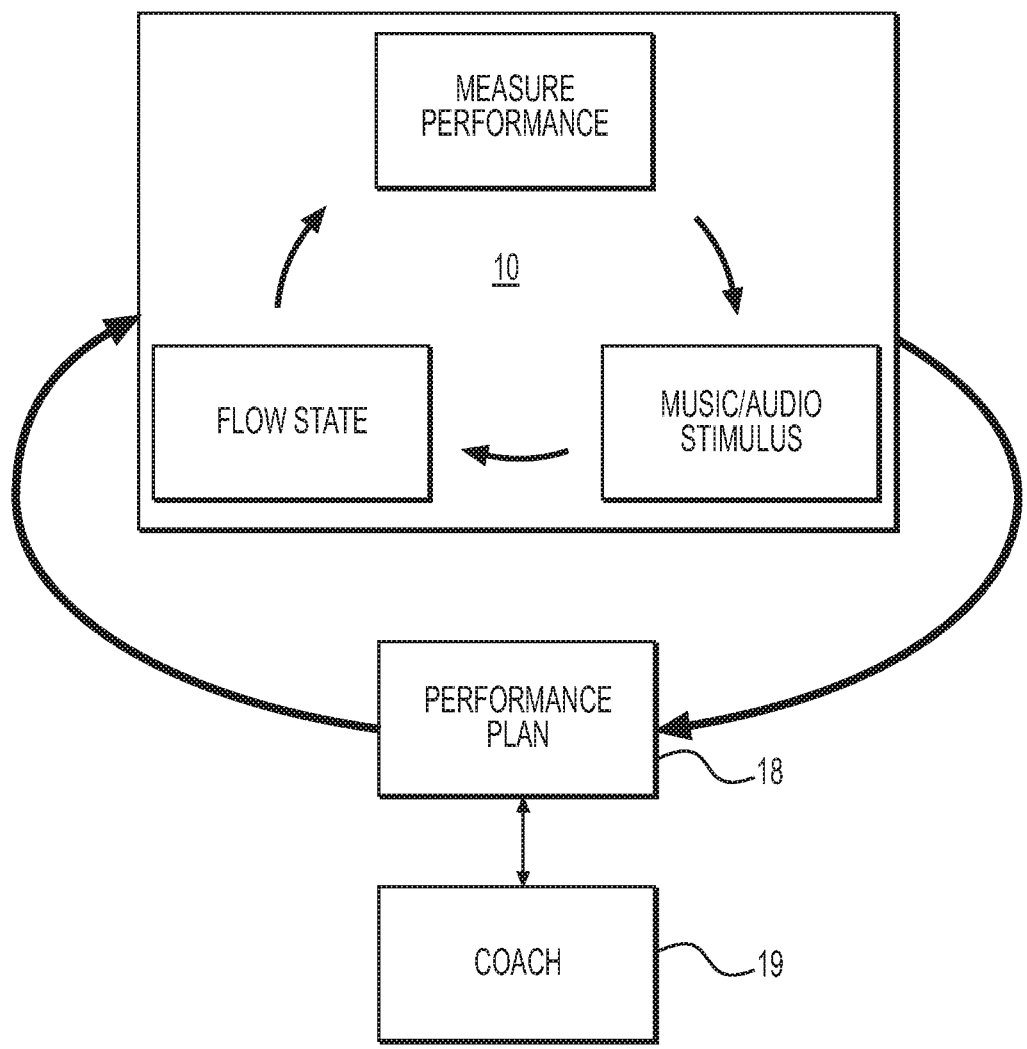

Reference will now be made in detail to exemplary embodiments of the invention, examples of which are illustrated in the accompanying drawings. Wherever possible, the same reference numbers will be used throughout the drawings to refer to the same or like parts.

Systems

Modern software applications or "apps" are also widely available that serve as music identification and music referral engines. Online services such as SHAZAM® rely on a technology known as acoustic fingerprinting to identify a song with reasonably high accuracy based on sampling it using a smartphone microphone or other device, processing the sample into a pattern and then matching that pattern to patterns stored in a database containing hundreds of thousands of songs. Acoustic fingerprinting can identify songs, but cannot itself suggest songs that a user might like. PANDORA® is a widely available online listening service that allows a user to input a "seed" song to create a "station." Based on the "genetics" of the inputted song, PANDORA® can consult a vast "genomic" database of songs scored for numerous musicological attributes, and create a playlist for the user of songs that the user is predicted to also like based on the "seed." Other listening services such as SPOTIFY® have "more like this" recommendation features that work differently, historically based on collaborative filtering but recently described as being redeveloped using deep learning approaches on convolutional neural networks. Wavelet-based approaches, such as wavelet packets, have also been investigated for music selection. See J. Berger, R. R. Coifman, and M. J. Goldberg, *Removing Noise From Music Using Local Trigonometric Bases And Wavelet Packets*, J. of the Audio Engrg. Soc., vol. 42, iss. 10, pp. 808-818, 1994.; see also R. R. Coifman and N. Saito, *Selection Of Best Bases For Classification And Regression*, Proceedings on Information Theory and Statistics, 1994 IEEE-IMS Workshop (1994).

The use of biomedical information in athletic training contexts has been explored, such as the use of pulse-oximetry. See D. Berry et al., *Educating the Educator: Use of Pulse Oximetry in Athletic Training*, Athletic Training Education J., vol. 7, iss. 2, pp. 74-80 (April-June 2012).

With this unprecedented flood of raw data and functionality, provided by smartphones, wearable technology, and their associated software apps, the modern user is nevertheless left without a great deal of actionable information about how to optimize his or her performance. Almost everything is left to a user in pursuit of a performance goal to sort out how to use the data from these various tools in the hopes that the surveillance will reveal that he or she is "doing something right." The approach to performance optimization nevertheless remains mired in the ancient principles of trial and error, and is rooted in a user's current mood, perception, and memory—each of which are subjective, unreliable and subject to conscious or unconscious modification.

Headphones

Modern audio hardware and software provides myriad varieties of sound systems, from personal devices to public address systems. Personal systems can include in-ear earbuds, such as the SKULLCANDY® 50/50, sport earphones for athletic or recreational use such as the SKULLCANDY® CHOPS, headphones such as the SKULLCANDY® CRUSHER, wireless headsets such as the SKULLCANDY® PLYR, wireless speakers such as the SKULLCANDY® AMBUSH, and wired speakers. SKULLCANDY® products are available from Skullcandy, Inc. of Park City, Utah, USA. Audio players are available as stand-alone devices such as the ubiquitous APPLE® IPOD®, or bundled onto smartphones such as the equally ubiquitous SAMSUNG GALAXY® or other devices such as the ARCHOS 5 Internet Media Tablet available from Archos of Igny, France.

Figure 1D:
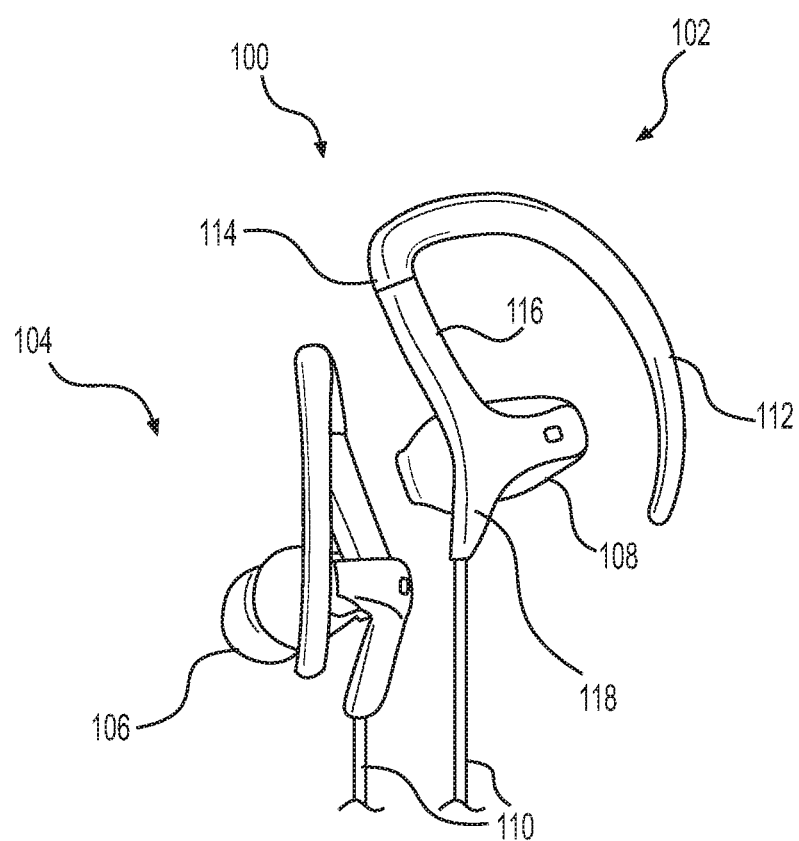
FIG. 1D shows exemplary earphones according to an illustrative embodiment.

As shown in FIG. 1D, an exemplary embodiment of headphones 100 can include individual in-ear acoustic phones, or earbuds, for the right 102 and the left 104 ears. The invention could be practiced by using over-the-ear headphones, or a single earbud. It is also contemplated that environmental speakers, public-address or other means of transmitting audio information could be used in appropriate settings. In the illustrative headphones 100, each earbud includes an earbud gel 106, which is inserted into the ear canal and helps to retain the bud inside the ear. The sound delivery mechanism can consist of multiple sound sources combined, such as two or more speakers in the earbud. The earbud may also include a local inward facing microphone, or a pressure sensor to assess the quality of fit, noise in the ear canal, acoustic impedance, or other parameters related to the parameters of the sound delivered to the eardrum. This quality of fit may be monitored through the entire time the user is wearing the earbud, and sound characteristics changed (within the same sound stimulus) to assure that the actual sound level and frequency delivered to the eardrum remains consistent despite mechanical and acoustic fit changes over time. The earbud gel is mounted on housing 108, which in illustrative embodiments can contain one or more audio drivers, e.g., speakers, and/or one or more microphone pressure sensors and processing electronics and, in some embodiments, sensors as described below. Cables 110 connect the headphones 100 to an associated audio source in some embodiments, although wireless reception via BLUETOOTH® or other wireless communication protocol is contemplated. The cables 110 can also be provided with controls (not shown) for manual adjustment of various features contained on the headphones 100. Controls for a connected audio source, such as song skipping, rewind, fast forward, volume, etc., are conventional controls. Additional controls can be provided to activate or deactivate various sensors as described below, as well as to mark certain events for future reference, such as when the headphones 100 wearer is achieving or not achieving a predefined subjective or objective performance goal, etc.

In the illustrative embodiment, headphones 100 are provided with ear hangers 112, which can be connected via swivel hinges 114 to housing extension 116 in known fashion. The hangers and/or housing extension can contain the processing circuitry of the headphones 100 as well as the various sensors described below. A cable extension 118 of the housing 108 provides an entry point for external cables 110, as well as space for processing circuitry and sensors. Alternatively, the sensors can be disposed in the housing 108 of the earbud, or in other retention features (e.g., stabilizers, wings, headbands, etc.).

In an illustrative embodiment of headphones 100 an amplifier is provided to provide tactile or haptic stimulation to the user. This can be achieved using bass acoustic frequencies from the audio drivers or speakers in the headphones 102 and 104, or a separate vibrator can be provided in the headphones 100 or externally as a separate peripheral (not shown).

Sensors

Wearable technology is also widely available. While being carried by a user, the smartphone provides a huge array of sensors and data collection potential. In an APPLE IPHONE®, for example, the display responds to multiple touch sensors. A proximity sensor turns off the display and the touchscreen when the phone is brought to a user's ear. An ambient light sensor adjusts the display brightness. A 3-axis accelerometer senses the orientation of the phone, which allows the display to change from portrait to landscape orientation, and is used for gaming controls. A magnetometer is used to drive the compass app, for example. The orientation of the IPHONE® can be completely characterized by reference to the accelerometer and magnetometer. A gyroscopic sensor helps characterize how the device is moving. Assisted GPS technology provides accurate terrestrial location data. The IPHONE® 6/6+ also contains a barometer, for measuring ambient atmospheric pressure. Other wearable technology products include the FITBIT SURGE®, available from Fitbit, Inc. of San Francisco, Calif., USA. The FITBIT SURGE® is a wireless-enabled activity tracker packaged in a wristwatch-style form factor. The FITBIT SURGE® contains 3-axis accelerometers, a gyroscope, magnetometer, ambient light sensors, GPS and a heart rate monitor. It also incorporates smartwatch features tying it to other functionality of a smartphone, such as Caller ID, text alerts, and controls for a music player.

Various sensors are contemplated in illustrative embodiments described here. The sensors can be mounted on or in the headphones 100, or can be present in or on other devices usable with the present invention, e.g., smartphones such as the APPLE IPHONE® or SAMSUNG GALAXY®, activity trackers such as the FITBIT SURGE®, or as separate sensors wired to or networked within the invention's system. In the following descriptions of the components in the system below, it is to be understood that the singular can mean the plural and vice versa, unless specifically described to the contrary.

Figure 2A:
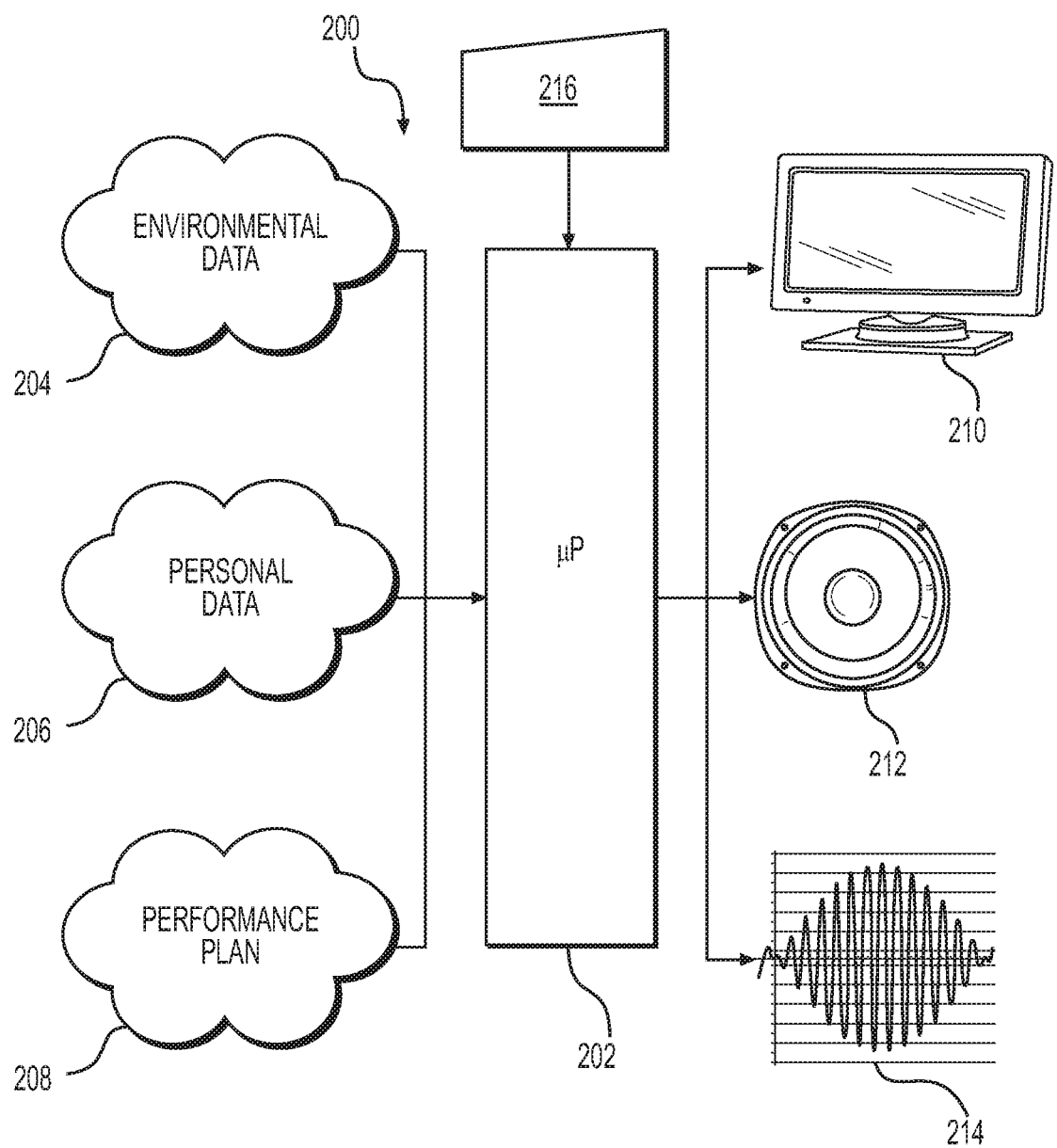
FIG. 2A shows an exemplary system according to an illustrative embodiment.
Figure 2B:
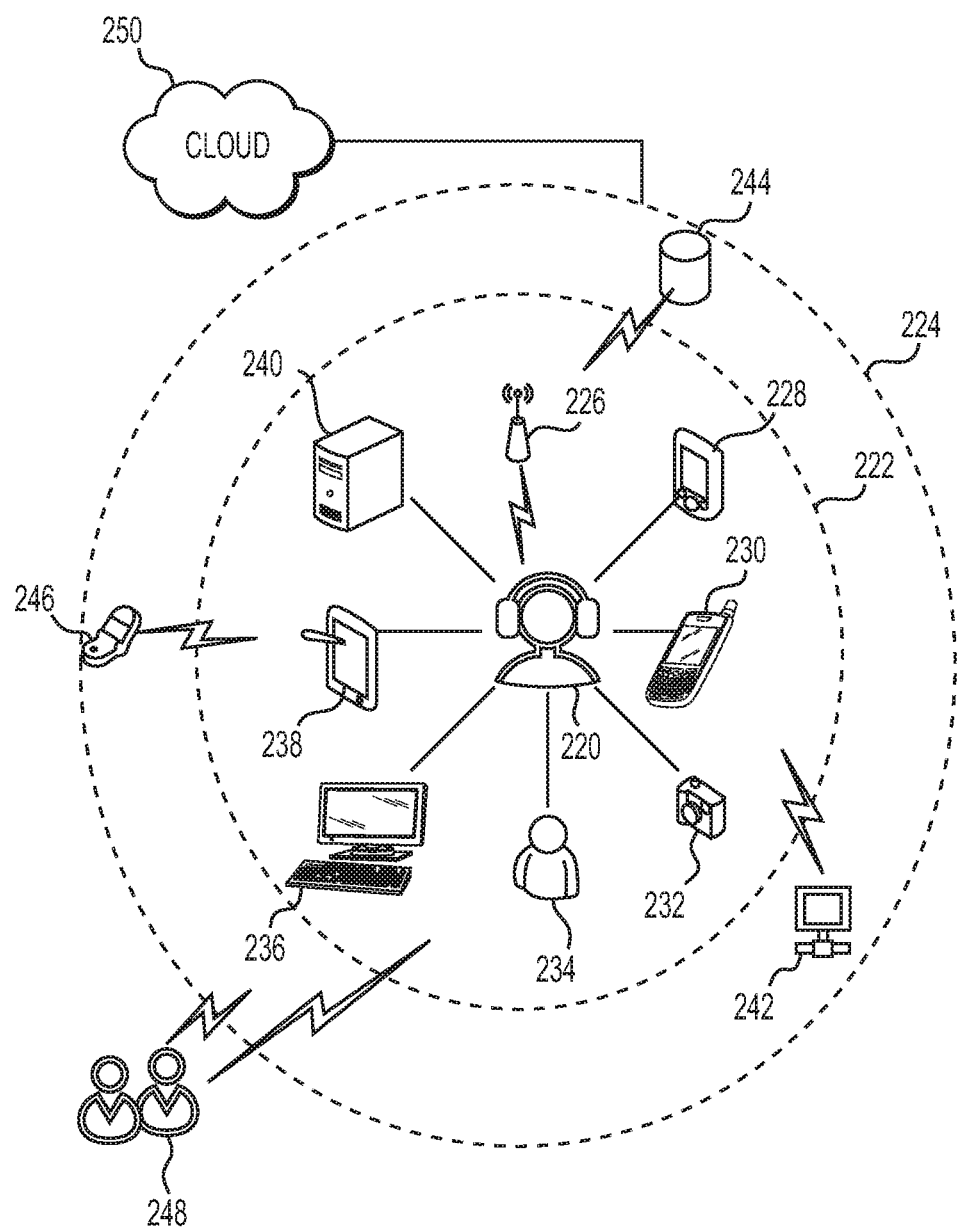
FIG. 2B shows an illustrative ecosystem employing the system(s) of FIG. 2A.

At one end of the spectrum of functionality, the headphones 100 of FIG. 1D can be configured to be self-contained, that is having all of the audio delivery hardware, telecommunications capability for data input/output and related processing, processing capability for control of audio delivery and sensor control, and a power source. At the other end, the headphones can be prior-art conventional headphones configured only for audio delivery, such as the SKULLCANDY® CHOPS in-ear buds, and the related functionality is obtained by other devices in the system. FIG. 2A depicts the various components of system 200 functionally, without regard to form factor, and FIG. 2B depicts the ecosystem in which system 200 dwells according to an illustrative embodiment. The system 200, in broadest terms, can comprise one or more microprocessors 202 for processing one or more inputs. These inputs, described further below, can include environmental data 204, personal data 206 and/or a performance plan 208. The one or more microprocessors 202 can provide one or more outputs, which can include visual output 210, audio output 212 and/or tactile output 214. In an illustrative embodiment, visual output can include text messages via SMS, e-mail or other protocols sent to an adequately configured receiving device.

The ecosystem of FIG. 2B shows user 220 at the center. A local sphere 222 contains the user 220 and elements of the system 200, discussed in greater detail in relation to illustrative embodiments below, which are generally within the proximity of the user 220. Global sphere 224 contains local sphere 222 and also networked resources, discussed further below.

Within the local sphere 222 with the user 220 is a network connection node 226, which can be cellular, WiFi, satellite, or wired for stationary users. The network connection node 226 permits communication with the global sphere 224, remote trusted parties 248 and cloud-based resources 250. Other functionality within the local sphere 222 can be connected wirelessly or via wired connections to the user interface. Wearable sensors 228 can be provided separately, on a smartphone, on wearable technology such as on headphones 100. Smartphone 230 provides multifunctional support as a personal data assistant, as a communication device or as a networked resource. Camera 232 provides image data. Manual input 234 permits user-provided data, to enter to local sphere 222, or data provided by a local trusted party. A computer 236 and a tablet 238 can also be provided for input and output as well as processing functions. A local database 240 can store environmental data 204, personal data 206 or the performance plan 208, as well as various other data required by the system 200.

The global sphere 224 includes networked resources, including the internet, including local- and wide-area networks 242, networked databases 244 and messaging capability 246, including e-mail, text messaging (SMS) or messaging via other communication protocols.

As further shown schematically in FIG. 2B, the ecosystems includes trusted parties 248 and the cloud 250. The cloud 250 is shown connected to the global sphere 224, but is available to connected resources in the local sphere 222 as well. Cloud 250 includes centralized data processing and storage capabilities, and permits enhanced data aggregation over several users 220. Trusted parties 248 include custodians of performance plan 208, and also credentialed individuals who can access either the global sphere or the local sphere of a system, or both. In illustrative embodiments, the trusted parties can be coaches, trainers, team members, parents, mentors, educators, advisors, supervisors, military commanders, etc.

Returning to FIG. 2A, manual input 216 is also possible in an illustrative embodiment, for a user to modify or override inputs 204, 206, 208 or outputs 210, 212, 214 or provide other controls such as audio playback control, sensor selection or override, etc. Manual input 216 can be used to link the system 200 to external databases or devices, supply information such as medical history and medications taken by the user, and other information for inclusion in the performance plan 208. Manual input 216 refers broadly to local inputs from the user, and can take place using known peripheral input devices such as keyboards, track wheels, touchpads or touchscreens, smartphones, mice, headphones or wearable inputs (e.g., buttons, physical or "soft") etc., in a known manner. Manual input 216 can also include verbal or vocal inputs. These inputs can interface with a knowledge navigator application, such as the SIRI® application by APPLE®. A natural language user interface can be provided to process vocal inputs from manual input 216, or from microphone inputs included in environmental data 204 or personal data 206. For example, a user could request historical performance data for comparison to current performance at a similar location, or other context. It is also envisioned that verbal commands contained in the performance plan 208 could be executed via the knowledge navigator to execute local commands on the processor 202.

For example, the performance plan 208 could contain a recording of a coach speaking a command that is played and results in execution on the knowledge navigator. The knowledge navigator can also be used to call on other networked resources, for instance, web pages. For example, a runner could verbally request the location of the nearest pharmacy while in the midst of a distance run.

In an illustrative embodiment, a performance plan custodian or other trusted party given access to the system 200 can directly access outputs in real time. For instance, a coach can provide an audio message to a user at a moment where immediate intervention is indicated. The system can incorporate such interventions in adaptively modifying the performance plan 208.

An illustrative embodiment is described with respect to a performance plan for a single user, but it is to be understood that the same concepts can be applied in a team context. Every member of the team can be given the same basic performance plan, but execution of the plan by microprocessor 202 could result in different outputs being selected for that particular user. As will be understood, the outputs selected are specific to a particular user in a specific context.

Environmental data 204 pertain to the location of the user whose performance is being monitored. In many instances, a GPS sensor can provide geographical location data, and that data can be used to obtain other data correlated to that location. For instance, the GPS coordinates N40.724167N, W111.539731 would locate a user at 1441 W. Ute Blvd in Park City, Utah. A simple call function using internet information resources could provide real-time weather information, such as the temperature, precipitation, cloud cover, wind speed and direction, sunrise and sunset times, humidity. Weather alerts and warnings can also be obtained real-time, or forecasts weighed in the implementation of a performance plan. Derivative information includes ambient light conditions, wind chill, icing conditions, flooding, etc. Based on trending of the GPS coordinates, it could be determined that the user is stationary or indoors. When correlated with personal data, described below, which can include lifestyle habits, it could be determined that the user is in a workplace, or a favorite fast-food restaurant, or a gym or training facility, and therefore not subject to ambient weather conditions. Each of these indoor locations, however, will have a different impact on a training program. Reference to the user's calendar on a smartphone or on the cloud 250 by processor 202 can also provide useful contextual information. Beacons, or other signal-emitting resource of known location, placed by a variety of third parties at select geospatial locations, can also be useful in determining location or contextual information.

In an illustrative embodiment, sensors are provided to provide measured values for some or all of the environmental inputs. For example, a magnetometer can provide compass headings to calculate direction or orientation. An ambient light sensor, IR sensor or UV sensor can provide exposure data to sunlight or artificial lighting conditions, sun warming and UV exposure. A temperature sensor, such as a thermopile, can provide body temperature and/or ambient temperature information. A barometric pressure sensor can provide GPS and indoor/outdoor navigation enhancement, weather forecasting, altimetry, as well as user spirometry data. A humidity sensor can provide atmospheric humidity data. An external microphone can provide ambient noise information to help discriminate an ambiguous location determination, for example, when the user is at a resort address, by providing sound profiles consistent with a concert venue, the system will know the user is not at the spa located at the same address. An oxygen sensor can provide ambient $O_2$ concentration, which can be combined with personal data to determine performance plan implementation.

The above list of sensors is not intended to be exhaustive, but illustrative. It is generally contemplated that a comprehensive description of a user's environment can be obtained or derived based only on partial inputs, or based on the user entering his or her location manually, with any data not obtained by measurement to be provided via a wired or wireless connection to databases, online or otherwise.

Personal data 206 pertain to the bodily movement, orientation and performance of the individual being monitored. Accelerometers can be provided to measure the magnitude and direction of accelerations, as well as vibrations. Accelerometer data can be used to calculate user movement, such as footsteps (i.e., a pedometer), the speed and distance of a run or the characteristics of gait (e.g., stance and swing phase). In contact sports, accelerometers can provide impact data. Accelerometer data can also be used to calculate a freefall of a user, which can be useful during training involved in aerial skiing, freestyle snowboarding, trampoline, gymnastics, surfing, skateboarding, etc. A gyroscope can provide data useful in calculating orientation. Combined with accelerometer and magnetometer data, the orientation of a sensor device, and thus possibly the user (when the orientation of the user vis-a-vis the sensors is known) can be calculated. When the sensors are located in headset 100, in one or both of the earphones 102, 104, the orientation of the user's head can be ascertained. A gyroscope is typically based on one or more oscillators that detect angular acceleration about three-dimensional axes. Gyroscope data can be useful in determining postural orientation and stability, balance, flight or trajectory orientation, and the rate of change of these. Separately or in addition, a set of pre-defined or user-defined movements or gestures can be captured as data input.

Various other personal data sensors are also found in an illustrative embodiment. Pulse oximeter (pulse-ox) data is useful for showing a user's oxygen saturation ($SO_2$). A pulse oximeter operates by passing light beams of known wavelengths through thin tissue in the body, and variances in absorbance are processed to correlate to the oxygenation level of pulsating blood. The fingertips are a conventional location for pulse-ox sensing, as is the ear. Headset 100 and ear hanger 112 provide locations for a pulse-ox transmitter and receiver in one illustrative embodiment. Although $SO_2$, may not be useful as a measure of fatigue or exertion alone, it can be a helpful indicator of the onset of chronic over-exertion fatigue which can impact a training program, or indicate the need for rest to achieve full recovery. $SO_2$ also can help signal a user's altitude acclimatization (or lack thereof), or flag health-related conditions such as anemia or pre-symptomatic bronchitis. Long term changes of $SO_2$ over the course of, e.g., several months of training can be observed. The pulse-ox device also itself measures heart rate information, which can be used as a pulse measure alone of in the monitoring of heart-rate variability (HRV) as discussed below.

Heart rate alone is a useful indicator of exertion. Optical sensors or acoustic sensors can be located on headset 100 to gather heart rate data alone, apart from any pulse-ox sensor. Different exercise intensities as correlated to heart rate have different effects on the body, and can therefore serve as targets for training. The rule of thumb for determining maximum heart rate is as follows:

$$R_{max} = 220 - \text{age} \qquad \text{Eq. 1}$$

Exercising at 60% of $R_{max}$ for example, predominantly targets the aerobic system in most people, and during aerobic exercise for a long enough duration, the major source of fuel will be from fat. This level of intensity is therefore indicated by those wanting to lose weight and achieve general conditioning. A heart rate training zone of 70-80% of $R_{max}$ will still predominantly target the aerobic system, but in conditioned athletes the main source of fuel will be glycogen, which is derived from metabolized carbohydrate. In an illustrative embodiment, the performance plan 208 can contain a target heart rate. Using the example of a 25 year-old conditioned runner, $$R_{max} = 220 - \text{age}$$

$$R_{max} = 220 - 25$$

$$R_{max} = 195$$

$$(0.7)R_{max} = 136.5$$

$$(0.8)R_{max} = 156$$

The performance plan according to an illustrative embodiment would therefore establish a heart rate training target of between 137 and 156 beats per minute while engaged in aerobic training involving running. Other sports might use different thresholds and equations for calculating maxima, but this illustrative example is instructive.

The variability in resting heart rate (HRV) is also a useful diagnostic of overtraining, which would indicate a need for rest toward a full recovery. However, there is no direct correlation, and an elevated resting heart rate could merely mean the user is watching an exciting movie. This is when other situational or environmental information 204 would be helpful to analyzing a user's personal data 206, or when trends in personal data 206 could be exploited. For example, if an accelerometer or activity sensor indicates the user is at rest, but the GPS coordinates indicate the user is at a movie theater, then the resting heartrate measurement may not be reliable as a diagnostic. Resting heart rate is ideally measured either during sleep or first thing in the morning, before getting out of bed. The accelerometer and gyroscope sensors could be used to detect a prone position, or the alarm app on a linked smartphone could be used to indicate a sleep period. Day-to-day variations in resting heart rate of approximately 5% are common and not correlative with over fatigue. Increases of greater than 5% are typically reported in fatigued or acutely "over-reached" or "under-recovered" individuals showing signs of sympathetic nervous system stimulation. Ensuring the proper "de-stressing" of a user is used in an illustrative embodiment to ensure the most effective training plan 208.

HRV can also be calculated from impedance measurements. Sensor data representative of skin impedance can be used to measure HRV. See T. Thong, et al., *Correlating Heart Rate Variability with Skin Impedance Measurements*, Engineering in Medicine and Biology Society, 2005, IEEE-EMBS 2005, 27th Annual Int'l Conf. Proceedings, pp. 4947-4950.

A close relationship between attention and HRV has been demonstrated. See M. Coles, *Cardiac and Respiratory Activity During Visual Search*, J. Exp. Psychology, no. 96, pp. 371-379 (1972). Changes in stimuli also cause transient or short term changes in HRV. See E. Porges et al., *Heart Rate Variability: An Index of Attentional Responsivity in Human Newborns*, Developmental Psychology, no. 8, pp. 85-92

(1973); M. Orim, *A Method for Continuously Assessing the Autonomic Response to Music Induced Emotions Through HRV Analysis*, Med Biol Eng. Comput. 48:423-433 (2010). Relaxation following exercise can also be influenced by auditory stimuli. See P. McConnell et al., *Auditory Driving of the Autonomic Nervous System*, Frontiers in Psychology, vol. 5, art. 1248 (November 2014) pp. 1-10. In an illustrative embodiment, a change in HRV accompanying a change in stimulus may indicate that the athlete is responding to a stimulus, such as a change in sound stimulus or music. The microprocessor 202 can compensate for variables, such as different levels of exertion, and in different states of flow, which can have an impact on the HRV measurement.

Relaxation is an important component of recovery during training. Relaxation is also an important precondition for the achievement of flow as discussed above. EMG sensors or strain gauges can be used to measure muscle tension in the body. Tension in the jaw can be measured in an illustrative embodiment from a sensor mounted in headset 100. EMG signals can be used to measure tension as a measure of relaxation, achievement of recovery, or overall levels of stress in daily routines (when not eating). The sensors can also be used to detect eating activity. The EMG data can be used to provide biofeedback to help a user modulate the tension and achieve a desired state, e.g., relaxation. Other points on the body can be monitored using separate sensors.

Sleep interval data can also be used to implement a performance plan 206. Accelerometer and/or gyroscopic data as well as manual inputs or calendar cross-referencing from a smartphone or other networked resource can help the system 200 determine when a user is sleeping. Environmental data 204 can then be monitored for optimal sleep environmental conditions, such as background noise, ambient light, and ambient temperature. Each of these parameters can be dictated by the performance plan 208, or rely on standard recommended values. During sleep, frequent movement could indicate an uncomfortable bed, and the microprocessor 202 could send an output to the performance plan custodian, e.g., a coach, or the user to shop for new mattress or switch to hypoallergenic bedding. In an illustrative embodiment, if the user was near home, then the knowledge navigator of the system 200 could refer the user to a nearby bedding store or online resource to encourage compliance. A coach training a team of athletes at a residential training center could detect poor sleep patterns generally, indicating the need to replace bedding. The presence of environmental noise could indicate a need to adjust sleep schedules if the noise is cyclical. For instance, GPS data indicating the user's home near an airport might attempt to adjust sleep schedules to minimize noise based on flight pattern data obtained from an online resource. Excessive sensed ambient light which can interfere with sleep could result in the system 200 sending an output reminding the user to close the curtains, adjust the sleep schedule to later times of day, or to relocate a user's bedding to minimize light exposure during sleep intervals. The system output can serve as an alarm function for a user to terminate a sleep interval, with follow-up monitoring of patient environmental data 204, for example, accelerometer and gyroscope information or manual inputs 216 following a prompt to verify that the user is ambulatory.

Eye movement data can also be used in many human factor settings, and can also be used for drowsiness or fatigue detection. Eye movement sensors can be based on optical sensing or by using electrodes placed around the eye sockets. The data from eye movement sensors can be used as a measure of alertness, which could have an impact on a training program, or on daily activities such as driving. Research conducted by the Virginia Tech Transportation Institute has shown that 80% of vehicular crashes and 65% of near-crashes occur within three seconds of some form of driver inattention. See DOT HS 810 594, *The Impact of Driver Inattention on Near-Crash/Crash risk: An Analysis Using the* 100-*Car Naturalistic Driving Study Data*, January 2004. This observation is equally applicable to athletic performance, where a distraction could lead to an error in execution that could not only affect performance, but result in injury. In an illustrative embodiment, eye movement sensors are located on headset 100, or a separate device is included in the system 200.

Analysis of facial expression changes, referred to variously as micro-facial expression analysis or microgrimace analysis, is a modality for scoring emotional state, such as pain or agitation. See Bin Mansor et al., *Reckoning of Facial Grimacing Scheme for Patient Agitation in Critical Care*, Int'l J. of Res. and Revs. in Art. Intel., Vol 1, No. 1 (March 2011). In an illustrative embodiment, the personal data 206 can include image data, or features extracted from image data that correlate to mood states, such as relaxation or unease in the tracking of flow state. A performance plan 208 can then account for a user's physical condition and promote rest and full recovery in order to avoid suboptimal performance over the longer term, or injury from over training. Image features correlating to pain can also indicate the early onset of performance-robbing benign afflictions such as headaches, which if untreated can develop into distracting and even debilitating events. An early indication to a user via one of the outputs 210, 212, 214 to take an analgesic could help to optimize performance in an illustrative embodiment. Following the same concept, postural analysis of image data of a user could also be undertaken to detect fatigue or suboptimal biomechanics. Fatigue detection according to an illustrative embodiment could be used to alert drivers, for example, to a loss of concentration.

Brainstem Auditory Evoked Potential (BAEP) data are useful for determining neuronal activity in the auditory nerve, cochlea, brainstem and related structures. Frequently used to test neonates for deafness, sharp clicks or tones are administered to the ears and then the BAEPs monitored by surface electrodes. Shorter sensory-motor reaction times have been reported in athletes compared with sedentary subjects. Research measuring BAEPs have showed great differences related to gender, and differences were also found in relation to physical activity. BAEPs have been shown to be linked more widely to top-class physical activity, as opposed to specific sensory aptitude. See F. Martin et al., Int. J. Sports Med. 1993 November; 14(8) 427-32. In an illustrative embodiment, auditory stimulus is administered via headphones 100 or other auditory device, and BAEPs measured in response to the stimulus. This form of personal data 206 can be used as a measure of performance and achievement of performance plan 208 elements.

The P300 (P3) wave is an event-related potential (ERP) brainwave component that occurs in the process of decision making. The P300 isn't related to the stimulus per se, rather it signals that a subject has recognized a stimulus and is evaluating it. When a clear and confident decision is made, the P300 fires quickly. When equivocation occurs, the response takes longer. For this reason, P300 has been studied for application in lie detection. However, P300 response data in an illustrative embodiment is used to show clear decision making that can accompany peak training and preparedness, and flow. P300 can also be used to show mental recovery or lack thereof following a performance error, or an accident.

Research has shown that portable EEG devices are capable of reliably measuring P300 responses in a user. See M. De Vos et al., *Towards a truly mobile auditory brain-computer interface: exploring the P300 to take away*, Int J Psychophysiol. 2014 January; 91(1):46-53. In an illustrative evoked response sensors are provided to monitor P300 ERPs, which are supplied among personal data 206.

A microphone, as discussed above with respect to environmental data 204 can also serve as a user input device 216 as is known. The microphone, according to an illustrative embodiment, can also be used to collect speech or other oral sound data from a user in order to detect variance from past personal data, or from a norm. Speech pattern algorithms can also be provided to analyze a user's attitude orientation, and therefore his or her receptivity to coaching elements contained in the performance plan 208. For example, word choice by a user is often correlative to concepts of self-perception and worldview. Successful coaching in a performance plan involves relating to a user in a manner that facilitates performance improvement. See Smith, I. (2004) Deep Coaching—how to communicate more effectively with your athletes. Brian Mackenzie's Successful Coaching, (ISSN 1745-7513/13/June), pp. 1-4. Vocal tension can also be detected by speech pattern recognition algorithms, which can signal mood elements such as emotional stress. Emotional stress is a distraction from the achievement of flow, and therefore a performance plan may need to be modified to first facilitate the elimination of stress before focusing on the refinement of skill-based aspects of performance. Further, the presence of slurred speech or other characteristic patterns following an accident or collision, e.g., detected by other environmental data 204 or personal data 206 could signify a concussion or traumatic brain injury, indicating referral to medical care. While in an illustrative embodiment a coach for an athlete user is discussed, the concepts of the disclosure are equally applicable to other contexts of human performance, such as concentration training, meditation and relaxation practice, academic tutoring, professional mentoring, military training and parenting.

A microphone can also be employed to measure respiration rate. Respiration rate data is an important measure of exertion or overexertion as well as relaxation or stress level, and the acoustic profile of a user's breathing, compared to a standard or based on past measurements or benchmarks, can provide useful information for the performance plan. Variations in respiratory rate are also connected to attention level and stimulation. See, e.g., Coles and Orini. Respiratory rate and variation can also be measured using transthoracic electrical bioimpedance.

Capnographic (or capnometric) sensor data can help expose hyperventilation, which can trigger a wide array of performance-robbing symptoms in a user. A performance plan 208 can be implemented to attain the proper $CO_2$ level in expired breath to encourage optimal respiration.

Heads-up displays, such as GOOGLE GLASS® can serve as a visual output 210 and/or audio output device 212, and also provides a microphone, accelerometer, gyroscope, magnetometer, ambient light sensor, proximity sensor as described above. Golf-grip sensor gloves can provide performance data related to grip strength on a club. Connected helmets for motorsports containing heads-up displays, cameras and built-in GPS can also serve to provide data to the system 200. Sensors can be provided as smart watches, wristbands, armbands and headbands. Headbands can also provide EEG data. Tactile or haptic output 214 can take the form of clothing such as the FOXTEL ALERT SHIRT® or temperature control clothing such as the PROCOOL, bionic prosthetics such as those marketed by EKSO and BEBIONIC. Sensors can also be provided on clothing such as the OMSIGNAL®. Electrodes such as the SENSE PRO, and other wearable devices such as the MISFIT SHINE®, SMART CAP® from Edan Safe, BALANSENS and FITGUARD® each provide data that are usable within the system 200.

In any or all of the above sensors, MEMS and nanotechnology fabrication techniques can be employed in illustrative embodiments to achieve small, lightweight form factors. The above listing of sensors is intended to be exemplary and not exhaustive, and any combination of sensors in any number can be employed.

Nested Control Loops

An illustrative embodiment is here described that employs a control scheme involving nested control loops. Other control schemes are possible that are less or more complex, but the illustrative scheme employs nested control loops for a training program based on calendar divisions, i.e., days, weeks and months. Longer and shorter divisions are of course possible, but for illustration, the nested loops of FIG. 3 will be discussed here.

The training program process 300 starts at block 302. Decision block 304 checks an internal counter or calendar function or other indicia to decide if the program is complete. If the program is complete, the program stops at 324. If the program is not complete, the system enters smaller control loops. Decision block 306 checks to see if a monthly interval has ended. If YES, then a month counter is incremented at decision block 308, and the process returns to outer loop decision block 304 to see if the program has now completed. Each nested inner loop continues in like fashion. Decision block 310 checks a weekly interval and if it has ended, a new weekly interval is commenced by incrementing week counter at 312. If a week is ongoing then the process continues. Decision block 314 checks a daily interval and if it has ended, a new daily interval is commenced by incrementing day counter at 316. If a day is ongoing then the process continues. Decision block 318 checks a training interval and if it has ended, a new training interval is commenced by incrementing interval counter at 320. If a day is ongoing then the process continues. Training process 322 continues until completion as the innermost loop, discussed in more detail below. Training process is an adaptive process in an illustrative embodiment, and not every training interval will be the same. The training process 322 is dictated by the performance plan 208 in an illustrative embodiment.

Of course, other modifications are possible, such as manual overrides and resets of one or more intervals, etc. Again, illustrative process 300 is designed to show that a performance plan 208 can be implemented using a plurality of nested loops, which when considered in the context of the control scheme described below renders the concept advantageously adaptable and powerful.

Control Loop Example

Process control as a science evolved in the late 19th century to solve the problem of automatic ship navigation. So-called PID (proportional-integral-derivative) controllers were devised to adjust the rudder of a steamship in order to maintain a desired course heading. PID controllers rely on a control loop where a manipulated variable is changed in order for a process variable to achieve a predetermined setpoint. Based on observations of the current error between the state of the system and the setpoint (i.e., the proportional error), the accumulated error until the present (i.e., the integral error), and a prediction of the error that will occur in the future (i.e., the derivative error), the manipulated variable can be changed to stably arrive at the setpoint. The PID controller was successful in eliminating overshoot, a situation where too sharp a correction is made to the manipulated variable and causes the process variable to swing past the setpoint. PID controllers are a useful theoretical model for control loops in industrial processes and software control.

Figure 3:
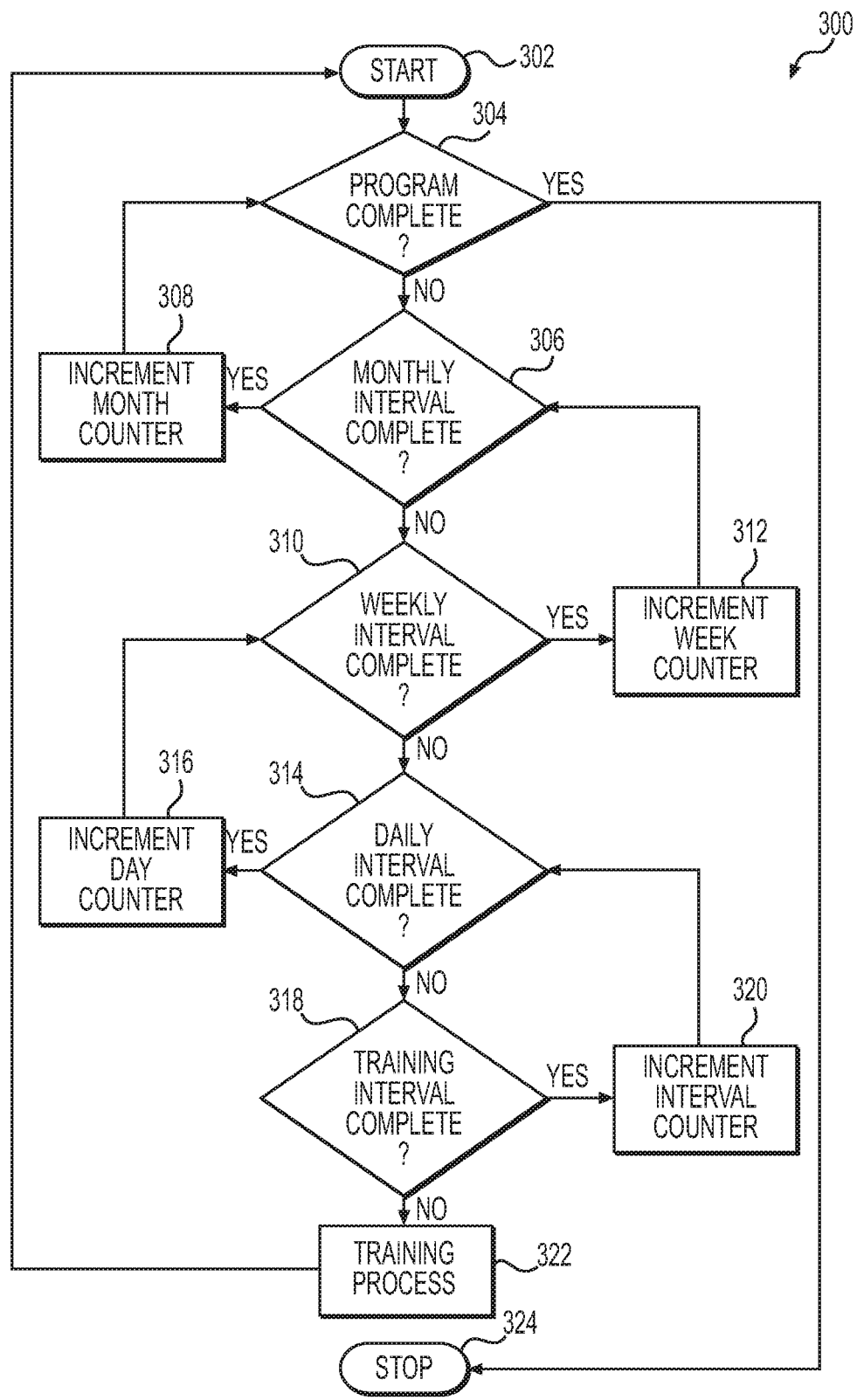
FIG. 3 shows exemplary nested control loops according to an illustrative embodiment.

In each of the nested loops described in reference to FIG. 3, data can be updated and the performance plan 208 updated to account for the various data collected. As discussed further below, certain features from the data can be identified as useful to achieve a particular performance goal, or setpoint, of a training process 322, That setpoint can be a long-term performance goal, such as the speed in which a marathon runner completes a 26.2 mile course, or a short-term performance goal, such as the achievement of relaxation and flow during a particular training exercise. Discriminant analysis techniques can be employed, described below, to identify variables in an applied stimulus, for example, a music or sound file, that correlate positively to the achievement of a desired performance goal. Before discussing this aspect of the system 200, the concept of feedback control will be useful.

In an exemplary embodiment, a PID control loop is used to provide stimuli to a user in a controlled manner, based on actual observations of the user and his or her environment in comparison to a performance plan. By adjusting the stimuli, which have been pre-categorized as correlative to the desired performance goal at issue, performance goals or setpoints can be achieved efficiently. The PID loop described here is used to drive an input, such as a performance metric, toward a setpoint or target value, and keep it close to that value by controlling an output, in the illustrative example audio stimuli. Similarly, a Kalman filter control algorithm can be employed for a more advanced closed loop system, along with many others (fuzzy modeling, neural network and genetic approaches, etc.).

Before continuing, it is worthwhile to mention that the use of music during training for athletics or studying for an academic exam is not new. Many athletes rely on inspirational music during training. However, the user is often relying on a static library of favorite music that may in fact provide a counterproductive stimulus, such as one stimulating more exertion at a time when overall performance could be maximized through a stimulus promoting relaxation and conservation of energy. In other words, what an individual likes to listen to may not, and frequently does not, capitalize on performance- and mood-modifying effects of music. The same is true for other audio stimuli, such as prerecorded messages, sounds of an athlete's favorite places in nature, sound effects and tonal combinations. The same is true for tactile or haptic stimuli. And to complicate matters, the same stimulus may not have the same effect on the user on different days, based on the myriad other environmental and personal data variances that occur during different times, as described by the different nested loops of FIG. 3.

Proportional-integral-derivative (PID) control loops approximate the human adaptive approach to environmental manipulation. PID control loops consider the current state of a system in relation to a desired setpoint (proportional), the accumulation of past error in the system (integral) and a prediction of future error of the system (derivative). When a person reaches for a pencil sitting on a desktop, he or she is unwittingly practicing a PID loop by analogy: the distance between the person's fingers and pencil represents the error state, and closing the gap to zero represents the desired setpoint. If the distance is great, the speed of movement of the fingers toward the pencil begins at a rapid rate (proportional). As the fingers get closer to the pencil, the person slows down the approach, based on visual and proprioceptive feedback, until the setpoint is achieved. In industrial process control systems, PID loops are described by the following equation:

$$u(t) = K_p e(t) + K_i \int_0^t e(t)\,dt + K_d \frac{de(t)}{dt} \qquad \text{Eq. 2}$$

where $u(t)$ is the output $K_p e(t)$ is the proportional component $K_i \int_0^t e(t)\,dt$ is the integral component, and $K_d \frac{de(t)}{dt}$ is the derivative component.

An industrial controller can use some or all of these components. For example, a PD controller uses the proportional and derivative components, but not the integral. Such cases can be viewed as setting the gain on the integral component, $K_i$, to zero.

The proportional term is essentially equal to the proportional gain, $K_p$, times the error e(t) at the time of sampling. The error equals the difference between value of the monitored process variable and the setpoint, the desired value for the process variable. The proportional gain can be adjusted to provide the desired attack rate. As can be appreciated, a large gain combined with a large error results in a large value for the proportional term. As the error decreases, however, the value of the proportional term decreases proportionally, because gain is a constant. A proportional-only controller, therefore will tend to oscillate, and if the gain is too high, the oscillations can become unstable. Also, a proportional-only controller can never achieve the setpoint, because in that state error is zero, and the value of the proportional term is also therefore zero.

Figure 4A:
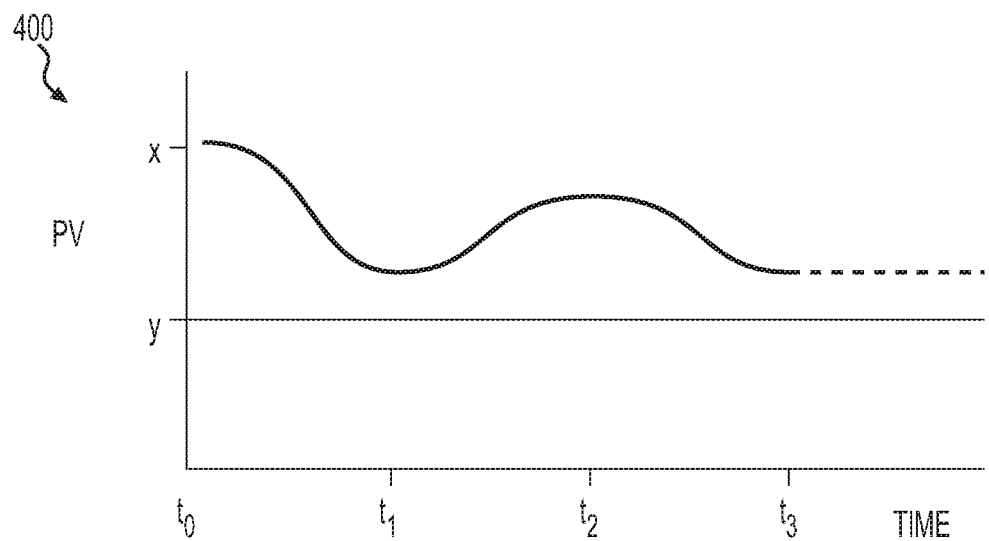
FIG. 4A shows an exemplary proportional feedback control scheme according to an illustrative embodiment.
Figure 4A:
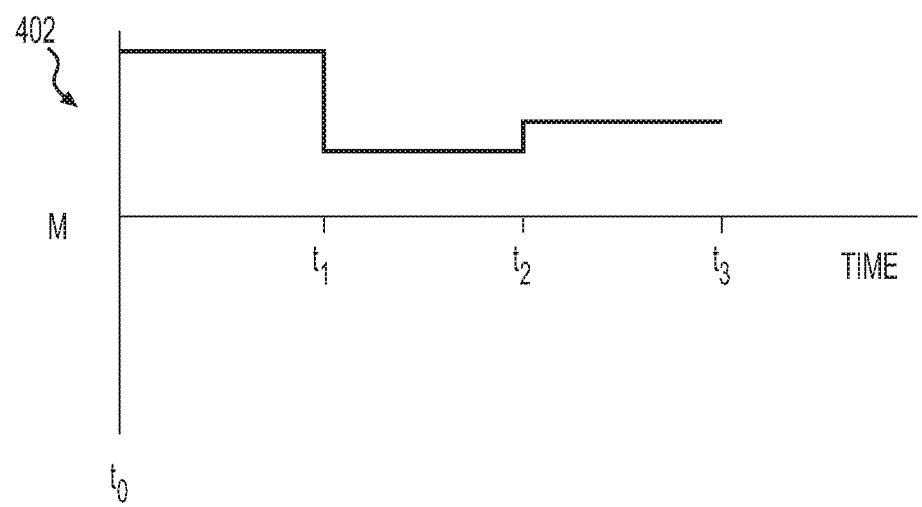

In an illustrative embodiment of a proportional-only controller, the action of which is graphically depicted in FIG. 4A, jaw tension is monitored as the process variable PV, shown on the upper graph 400. The output of a microprocessor 202 is an audio output 212, the content of which has been selected according to a selection algorithm, described in greater detail below. The audio output 212 has been classified and scored as having a meaningful correlation to relaxing jaw tension. The scored value of the audio stimulus is represented by the value M in the lower graph 402. In an illustrative process, jaw tension is sensed to be at a starting value of x at t=0, and the setpoint determined by the performance plan 208 is, during the illustrative interval, is y. The initial error, therefore is x-y, or the distance between these values on the PV graph. When the initial error is multiplied by the gain $K_p$ included in the performance plan 208, a corresponding value of M is obtained, which can be obtained from a look-up table or calculated. An audio stimulus matching the M value requested by the controller is then delivered to the user. The delivery of the audio stimulus in this illustrative example can be seen to cause jaw tension PV to drop, decreasing the error at $t_1$ between the current value and the setpoint y. Because the error has decreased, the proportional-only controller would calculate a smaller corresponding value of M and supply a stimulus having a correspondingly smaller scored value correlated to jaw-tension. At time $t_2$, it can be seen that the error has increased because of the change to a stimulus having a smaller M value. Again, the controller reacts providing a stimulus having a larger M value as the error increases, and the error decreases at time $t_3$. If the gain $K_p$ included in the performance plan 208 is too large, the system would oscillate unstably. If the gain is properly-selected, i.e., the controller is properly tuned, the system would eventually stabilize as shown by the dotted line in the upper graph 400 at a steady-state error known as the "offset." An offset is necessary because, as mentioned above, if the error is zero, the corresponding value of M would also be zero.

To eliminate the offset in a proportional-only controller, an illustrative embodiment includes an integral component, $K_i \int_0^t e(t) dt$. In most industrial components, accumulated error is based on a time constant that provides a smoothed value for the integral component based on the most recent errors, rather than a true integral of all error accumulated. This approach is simpler, and allows a single gain K to be provided by the performance plan, and the time constant r, to be specified as a tuning parameter. The resulting equation is for the exemplary proportional+integral (PI) controller is as follows:

$$u(t) = K_p e(t) + \sum \frac{K}{\tau_i} e(t) \qquad \text{Eq. 3}$$

Figure 4B:
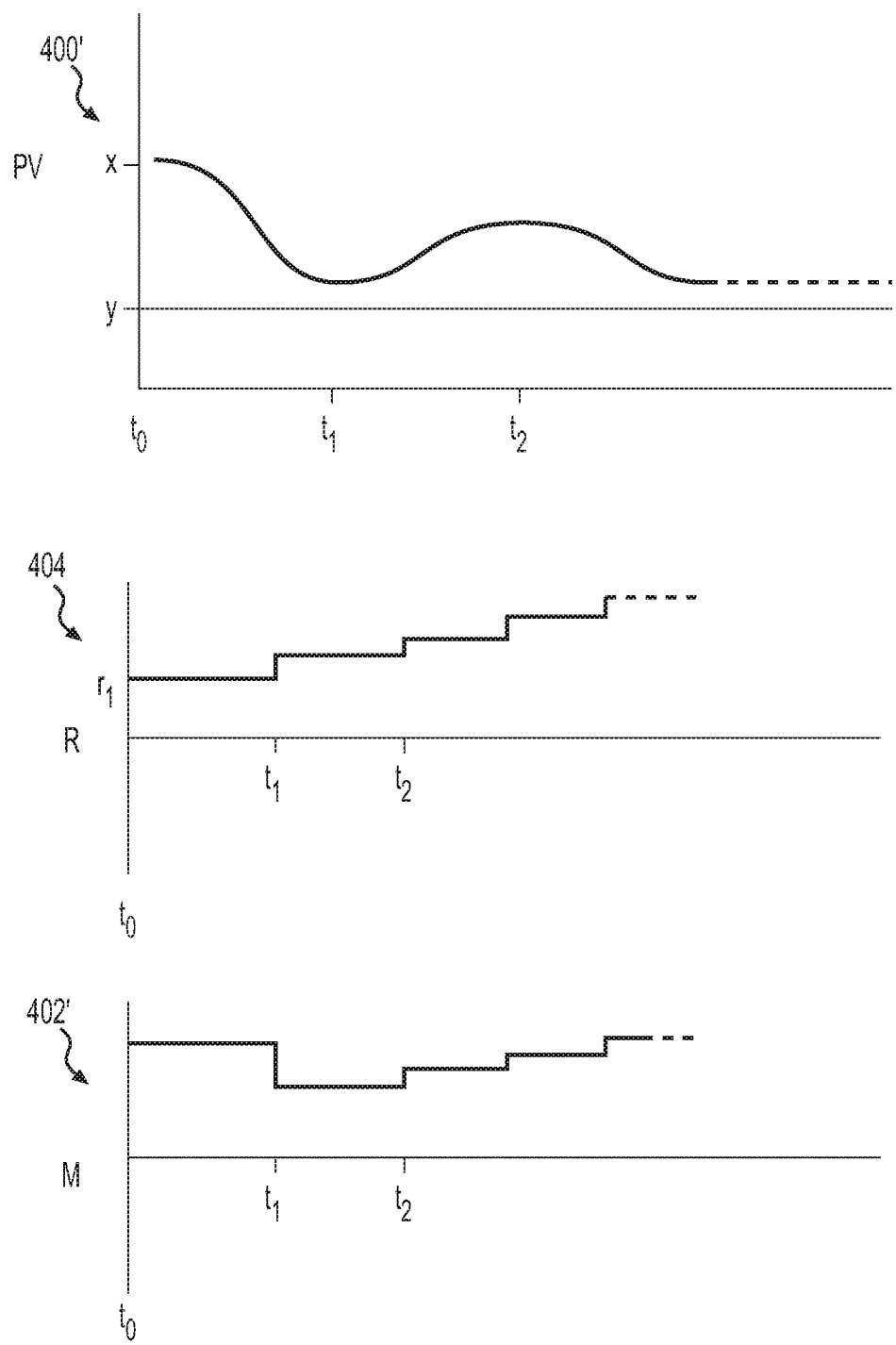
FIG. 4B shows an exemplary proportional-integral feedback control scheme according to an illustrative embodiment.

The summation term above is sometimes referred to as the reset register or simply the reset. Using the same illustrative example as above for the proportional-only controller, FIG. 4B illustrates the addition of a reset to form a PI controller. A middle graph 404 is added to display the reset value R. As shown, a proportional value of the error $r_1$ is stored in the reset register and added to the output of the controller along with the proportional value as above. The result is a higher output, and therefore a higher specified value for M than in the proportional-only controller. The error is therefore decreased more at time $t_1$ than with the proportional-only controller. The resulting error at time $t_1$ is then added to the reset, increasing it. The smaller error results in smaller proportional value, but that is partially offset by the increase in the reset value. The overall output, however, decreases in the illustrative example and a smaller specified value for M is requested by the controller. As time passes, the oscillations in the proportional component are offset by the reset register and overall error continues to fall, thus leading to a more stable value for M as jaw tension PV approaches the setpoint. Eventually the proportional component becomes zero as error "resets" to zero.

For further refinement to a proportional-only or PI controller, an illustrative embodiment further includes a derivative component, $$K_d \frac{de(t)}{dt}.$$

In most industrial controllers using the derivative component, the value of interest is how fast the error is changing, or the change in error divided by the change of time, resulting in a measure of slope of the error. This approach is simpler, and as with the simplifications for the integral component, allows a single gain K to be provided by the performance plan 208, and the time constant $t_1$ to be specified as a tuning parameter. The resulting equation is for the exemplary proportional+derivative (PD) controller is as follows:

$$u(t) = K_p e(t) + \frac{K}{\tau_i} \Delta e(t) \qquad \text{Eq. 4}$$

The derivative component allows a prediction of the error in the future, in order to apprehend a situation where the setpoint is overshot by the controller, where the process variable is changing too fast. In the illustrative embodiment, where the jaw tension of might respond slowly over time and therefore be said to have momentum, a large slope in the change of the error could indicate too aggressive a value for M, resulting in a correction value to be subtracted from the output of the controller. In another illustrative embodiment, the derivative value is based on the PV value, instead of the error, allowing changes of setpoints to be accommodated more adaptively. While overshooting jaw tension may not be perceived as critical to achieving training goals in an athletic context, too much relaxation could be more detrimental in other areas of human performance, such as academic studying. In other performance measures, such as cycling, where the process variable is velocity, exertion that leads to speeds in excess of that required for optimal performance would be essentially wasted, thus the derivative function could be more important for the performance plan 208.

Data Feature Selection and Discriminant Analysis

Discriminant analysis is a computational tool for detecting features in a data set that allow the researcher to discriminate between two or more naturally occurring groups. Discriminant analysis is also useful for classifying data into different groups. The former application is referred to as descriptive discriminant analysis, and the latter predictive. A simple example of the use of discriminant analysis described by Burns et al. in *Business Research Methods and Statistics using SPSS*, ch. 12, Sage (2008), involves the prediction of whether an employee is a smoker or a non-smoker. The data, called predictor variables, collected on each participant included age, number of days absent the previous year, a self-concept score, anxiety level and attitude toward a company anti-smoking workplace policy. Discriminant analysis in Burns' example showed that self-concept and anxiety were good predictors of whether an employee was a smoker, and age and days absent were poor predictors. A classifier could then be built on the significant predictors and "trained" with known data (i.e., smokers and non-smokers). The classifier in Burns' example was then used to predict new cases, which resulted in an accuracy of 91.8%.

When there are more than two groups, more than one discriminant function can be derived. For example, when there are three groups, a first function could be derived for discriminating between group 1 and groups 2 and 3 combined, and then another function could be derived for discriminating between group 2 and group 3. For example, we could have one function that discriminates between tobacco users and non-tobacco users, and a second function to discriminate between smokers and snuff users.

Canonical analysis is another computational tool useful when comparing two sets of variables to determine what is common among the two sets. Canonical analysis is useful in a multiple group discriminant analysis, so that there is no need to specify how to combine groups to form different discriminant functions.

Discriminant analysis is usually linear, and based on a normal distribution of the variable data. Linear discriminant analysis also assumes that the variance/covariance of the variable data is homogeneous across groups. When these conditions cannot be satisfied in linear space, such as when the data exhibits severe non-linearity, non-linear approaches can be applied. For example, the input space can be transformed to a high-dimensional feature space where a linearly separable distribution is present in the feature space. See e.g., C. Park et al., *Nonlinear Discriminant Analysis using Kernel Functions and the Generalized Singular Value Decomposition* CITE.

Classification functions, as distinct from discriminant functions, are used to determine to which group a new observation most likely belongs. In general, there are as many classification functions as there are groups. Classification functions compute classification scores for new observations, and the computed scores determine class membership for the new observation. Classification functions typically operate on some set of features extracted from the data about the system that is being analyzed. A variety of feature selection methodologies are in common use, and more recently genetic algorithms have been investigated for automated feature selection. See M. Eberhardt et al., *Automatic Feature Selection by Genetic Algorithms*, Artificial Neural Nets and Genetic Algorithms: Proceedings of the International Conference in Prague, Czech Republic, Kurkova, V. ed. (Springer, 2001), pp. 256-259. Separately, advanced mathematical processing of signals has been employed to derive new feature sets from existing data that may provide more information about the underlying system than the raw features measured alone. The field of feature creation, selection and classification is constantly developing, employing some advanced methods such as singular value decomposition, support vector machines, neural networks, and others.

In the preceding section, a processor using controller logic selected an audio stimulus scored and classified according to its effect on a process variable. The classification of stimuli into classes that are effective for influencing a given process variable and those that are ineffective can be achieved using discriminant classifiers. After classification has taken place, the members of the class can be scored for their effectiveness with respect to a certain process variable. Further advantageously, unclassified stimuli can be classified using a classifier built using known "training" data sets having known performance-affecting attributes with respect to the process variable, which will be discussed further below. The first step is to determine which features of a stimulus are relevant or effective in influencing a process variable, which in an illustrative embodiment are audio stimuli and human performance measures, respectively. The approach can apply to tactile, haptic, visual and other stimuli as well in much the same fashion.

The identification and quantification of features of music is the subject of musicology, which is beyond the scope of this disclosure. The MUSIC GENOME PROJECT serves as an example of the variables that can be attributed, where each song has hundreds of "genes" or attributes. Attributes include genre, melody, harmony, rhythm, form, instrumentation, sonority, lyrics, vocal gender, etc. Any one or more of these attributes could affect human performance resulting in a statistically meaningful change, but it is not known at the outset of a training program which stimuli will affect which performance variables, and in which direction.

Feature selection algorithms are known. Different feature selection algorithms are broadly categorized into three computational methods: filter methods which are primarily used for preprocessing data sets; wrapper methods which evaluate subsets of variables for their value as predictors; and embedded methods. Algorithms based on the Filter Model in general use ranking or correlation techniques and include the Laplacian Score, SPEC, Fischer Score, Pearson product-moment correlation, Intra/Infra-Class distance, ReliefF, Chi-Squared Score, Kruskal Wallis test, Gini, Information Gain, Mutual Information, FCBF, CFS and mRmR and others. Algorithms based on the Embedded model include LASSO, Bolasso, BLogReg, SBLMR and others.

In an illustrative embodiment, a sequential feature selection (SFS) algorithm is used to determine whether a given feature is relevant. As an example, in an illustrative embodiment, attributes of musical audio stimuli are analyzed to determine if they vary systematically between two categories. If any of the features so vary, then that feature is relevant. In this illustrative embodiment, the two classes are (1) impactful on resting pulse rate; and (2) not impactful on resting pulse rate. This is a simple example using few variables, but it is known that multivariate analyses over multiple intervals is possible using more sophisticated statistical approaches.

The first step is to form a training data set. The training data set will contain data records describing musical audio stimuli and its attributes, which could number in the hundreds in the case of a song stimulus, as mentioned above. The training data will also include resting pulse rate data for a user listening to the musical audio stimulus. The first goal is to reduce the dimension of the data by finding a small set of important features which give good separation of the audio stimuli into the two classes. Using statistical tools, each attribute is tested for its ability to form well-separated groups of the data, and features are subjected to a certain threshold in order to remain in contention. This pre-processing saves computational time during feature selection. The more records in the training data set, the more attributes can be ultimately accommodated. Using other statistical tools, such as the cross-validation misclassification error, can help determine the smallest number of features required for accurate classification. Principal component analysis (PCA) is another linear method for dimensionality reduction. In the illustrative embodiment, the number of features required is four, and are shown to be tempo, timing signature, musical key and vocalist gender.

A classification function based on tempo, timing signature, musical key and vocalist gender can then be run on an unclassified population of data, after validation. Validation consists of measuring the predictive ability of the classification function, and is best performed using a data that was not used for training, but whose class membership is known. Classifier performance is evaluated using measures of specificity (known negatives were predicted as negative) and sensitivity (known positives were predicted as positives). Of course, false positives (known negatives predicted as positive) and false negatives (known positives predicted as negative) are errors and impact overall accuracy negatively. Once validation has been achieved, unknown data can be classified and scored. In an illustrative embodiment, the classifier is probabilistic and calculates a confidence value associated with its choice, and because membership in the classes (1) and (2) in this example are mutually-exclusive by definition, the confidence value can serve as the score. The score can also be calculated based on statistical information, including the number of records in a dataset and the number of times a user has selected the stimulus manually. Scores can be adjusted based on user input such as when the user skips or overrides a musical audio stimulus manually. The score can also be modified as part of the performance plan 208. Scores can also be aggregated over multiple users, as discussed below.

While described in the illustrative embodiment in terms of a musical audio stimulus, the musical audio stimulus does not necessarily have to be a conventional song. The stimulus can be modified to provide the attributes determined to be most correlative to the desired performance setpoint. For example, the tempo of a song or its pitch or frequency spectrum could be modified to provide a derivative song that exhibited the attributes desired by the performance plan 208. For instance, a song could be increased in speed and/or have its bass frequencies augmented. Audio stimuli having different attribute strengths could be combined to form a composite stimulus, for instance, a melody and an environmental sound such as bird songs or sea waves breaking, or a sonic trigger of P300 responses, or a haptic/tactile feedback.

Figure 5:
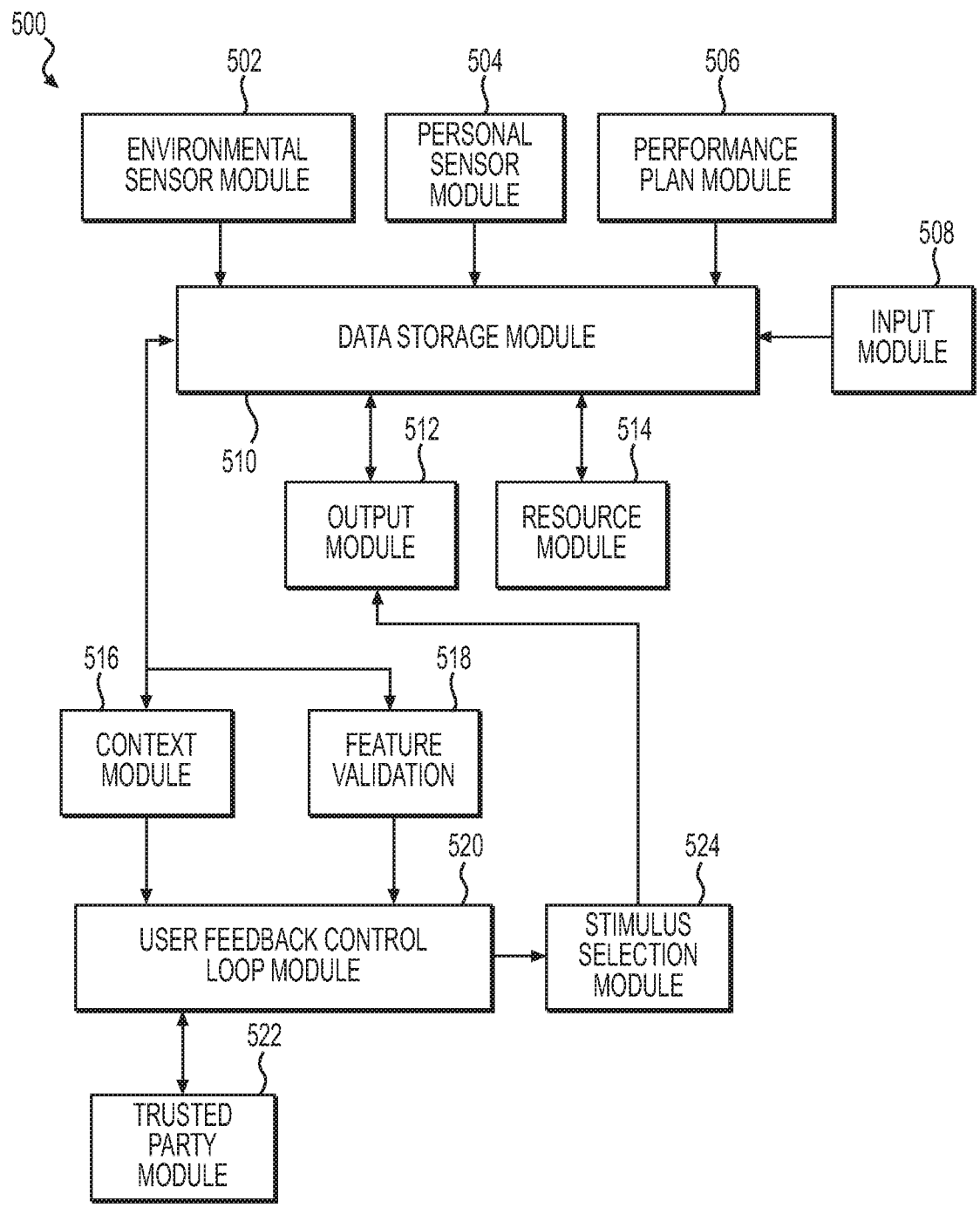
FIG. 5 shows an exemplary system block diagram according to an illustrative embodiment.

FIG. 5 shows an illustrative system block diagram 500. Each element represents any abstract type of processing which can include, for example, an in-memory function call, a system call, a database transaction, an external service call over a network, or some combination thereof. Each element can perform logic execution. Environmental sensor module 502 includes acquisition and management of sensors related to the environment in which the user dwells, including weather, temperature, ambient pressure, lighting, location, etc., as described hereinabove. Personal sensor module 504 includes acquisition and management of sensors related to the user, including performance metrics, movement and orientation data and biomedical metrics, etc., as described above. Performance plan module 506 includes a set of strategies, tasks and methods and related personal training profiles to achieve a personal performance goal. Input module 508 includes manual input acquisition and management of devices for obtaining non-sensor based information from the user, for example, using keyboards, touchpads, buttons or other input peripherals. Modules 502, 504, 506 and 508 are coupled to data storage module 510, either wirelessly or wired. Data storage module 510 can comprise a random access memory (RAM), a read only memory (ROM), a programmable read-only memory (PROM), a field programmable read-only memory (FPROM), or other storage device for storing data and software instruction code used by context module 516, feature validation module 518, user feedback control loop module 520, stimulus selection module 524 and other modules. Output module 512 is coupled to the data storage module 510, and includes formulating and providing outputs and management of output devices. Output module 512 can be a hardware component, a software program, or a combination thereof, allowing processed information to be displayed, portrayed, or signaled to a user via a wireless, networked or wired coupling. The output module 512 can allow correction, editing, deletion, modification or supplementation of output information. Resource module 514 is a software module that interfaces with a system central processing unit (e.g., processor 202 of FIG. 2A) and other system processes. Resource module 514 determines if there are data required from sources within the ecosystem of FIG. 2B, and manages the acquisition and management of data transfer protocols required for integration of the resource into the system. Resource module 514 is coupled to the data storage module 510. Context module 516 is a software component that receives data from the data storage module 510 and calculates a representation or model of the user's current state, including environmental and personal data. Feature validation module 518 is a software component that manages discriminant analysis and classification functions as described above. Feature validation module 518 is coupled to data storage module 510. User feedback control loop module 520 is coupled to context module 516 and feature validation module 518, and is a software component that manages the feedback features of the system, such as described above, related to the current personal data and environmental data, as compared to the performance plan. The control loop module 520 manages the delivery of stimuli to the user to increase or decrease current performance to attempt to closely match the parameters of the performance plan module 506. User feedback control loop module 520 is a hardware component, a software component, or a combination thereof. Trusted party feedback module 522 is coupled to the user feedback control loop module 520 and allows information related to the user's trajectory on a performance plan to be transmitted to a trusted party. Trusted party feedback module 522 also allows a trusted party to provide adjustments to the user feedback control loop module 520 to adjust parameters of the control loop, as described above. The user feedback control loop module 520 is also coupled to a stimulus selection module 524, a software component that identifies and selects a stimulus to provide to the output module 512. As described above, the stimulus is an audio or music stimulus that is determined to alter user performance, as modeled by the user feedback control loop module 520, in order to bring current observed contextual performance into conformance with the output of the performance plan module 506. Stimulus selection module 524 can also modify a stimulus based on the attenuation or amplification of features identified by the feature validation module 518.

Data Aggregation

As described above, various environmental data 204 and personal data 206 are processed by the processor 202 in accordance with a performance plan 208. The various inputs 204, 206, 208 can also be aggregated across numerous users in order to create larger databases of information that can be exploited.

A simple example, consistent with the illustrative embodiment described above, involves a musical audio stimulus. Over the course of time, whether or not a user is actively participating in the nested process 300 of FIG. 3, he or she could be wearing sensors, such as headset 100, and listening to music. The system 200 could advantageously monitor environmental data 204 and personal data 206 and warehouse it for pattern recognition and cross correlation and possible use in future performance plans. For instance, GPS, altimeter and velocity data may show a user is running uphill while listening to the radio when *Puff the Magic Dragon* by Peter, Paul and Mary begins playing. After a decrease in pulse rate and velocity, the user changes the channel. This data can, when subject to pattern-recognition and feature selection techniques as described above, be correlated to the experiences of other users encountering *Puff the Magic Dragon* in various environmental and personal contexts. When considered among a large population group, it might be identified that *Puff the Magic Dragon* has a statistically significant downward effect on pulse rate, and thus be well indicated for relaxation and poorly indicated for periods of strenuous athletic demand.

Identification of a music file without user input is possible using digital watermarking technology, such as DIGIMARC ID marketed by Digimarc Technologies or Beaverton, Oreg., USA or through acoustic fingerprinting used by SHAZAM®. In an illustrative embodiment, headphone 100 includes a microphone that can transmit song identification data to a data aggregator along with collected environmental data 204 and personal data 206 for aggregation and processing.

The data aggregator can be a storehouse for data from wearable activity tracking devices such as headphone 100, a FITBIT®, a JAWBONE UP™, and NIKE+FUELBAND®, ANDROID® WEAR, as well as smartphones and apps that gather or generate related data.

Virtual Coaching

Data aggregation can also assist in monitoring and refining performance plan 208. In an illustrative embodiment, a predefined performance plan 208 could be employed by other users, with their experiences aggregated to allow for modification or improvement of the plan. Top-tier athletes and their coaches could advantageously share their performance plans with other users, but illustrative embodiments in the context of athletics include performance plans contemplated for use by novices, local recreation leagues, scholastic athletics, collegiate athletics as well as Olympians and professionals.

The system 200 can also serve as a referral system to match a user with defined performance goals to a coach having experience or otherwise qualified to assist the user in achieving his or her goals.

In an illustrative embodiment, user 220 can signal a request for a trusted party 248 to temporarily provide performance training services on an availability basis. In an illustrative embodiment, an app-based network can receive coaching requests from a user, and then send these requests to available trusted parties. The network allows credentialed trusted parties to be available over a wide area to provide coaching, mentoring and training participation in a performance plan on their own schedule, and users can draw on these credentialed trusted parties from the cloud or other network. In an illustrative embodiment, a request for on-demand coaching or mentoring services is made on a computing device within the ecosystem depicted in FIG. 2B. An interface can be displayed, providing a plurality of options for providing the on-demand service, and providing a selection feature enabling a user to select a service option that is available to provide the on-demand service. In an illustrative embodiment, account, billing and financial transactional information can be provided and exchanged between the user and the trusted party providing on-demand services.

Example

In some embodiments, music/audio stimulus 14 can be modulated to effect changes in a user's performance, in some examples, a stimulus can be delivered to a user and various aggregated data can be measured to determine a flow state of the user, which can be accomplished with system 200. For example, standard music can be modified to produce a desired performance or relaxation change.

As one example, bass intensity of music can be modulated to alter HRV in a user. Modulation of bass intensity was investigated and significantly altered HRV. In the investigation, nine Division I recruited athletes (mean age 18.51±0.74 years, BMI 26.51±6.34 kg/m$^2$) were randomly selected from the Proactive Sports Performance training facility (Westlake Village, Calif.). Athlete competition sport varied across football, basketball, baseball and tennis. On two successive days, athletes were monitored to track physiological, recovery and performance measures during a standardized workout. Each athlete completed a workout consisting of nine exercises: vertical jump, treadmill sprint, single leg press, elliptical sprint, light bar bench press, pushups, chin-ups, rope jacks and arm bike pedal. Exercises were completed in the same order on both days. While exercising, athletes listened to a standard IPOD® playlist using METHOD® Earbuds provided by Skullcandy, Inc. (Park City, Utah), with one of three bass level interventions (low, normal, high; ±12 decibels). Bass level was modified on six of the nine playlists by Skullcandy engineers. The three remaining playlists contained unmodified music with a normal, unmodified bass level. Athletes in the experimental group were assigned a different level on each day, while three control athletes listened to the same level on both days.

Physiological and recovery measures were recorded using the Zephyr Physiological Status Monitoring system (Zephyr Technology Corp/Medtronic, Annapolis, Md.) and the Proteus Recover biometric monitoring patch (Proteus Digital Health, Inc., Redwood City, Calif.) (Table 1). Performance measures (jump height, velocity, reps, watts output, force) were recorded from respective exercise machines.

Figure 6:
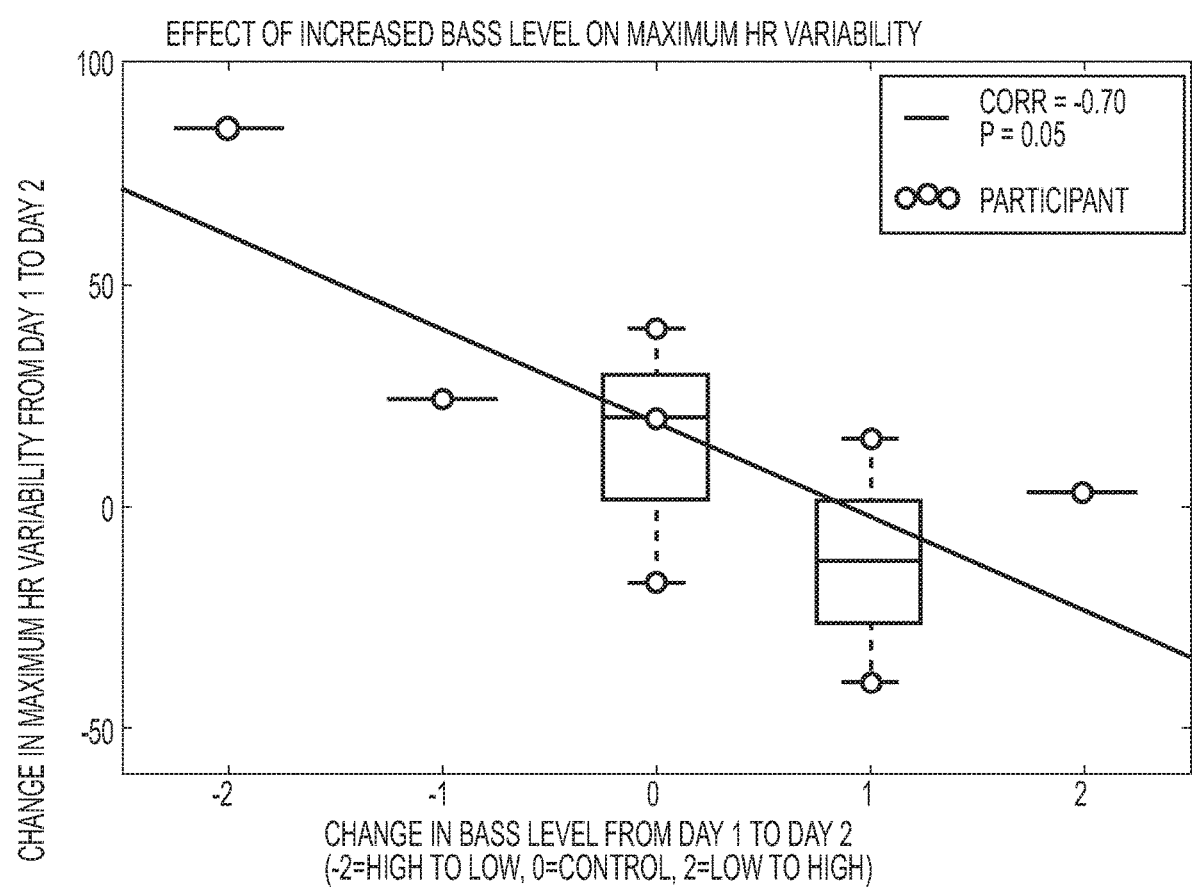
FIG. 6 shows the effect of increased bass level on maximum heart rate variability.
Figure 7:
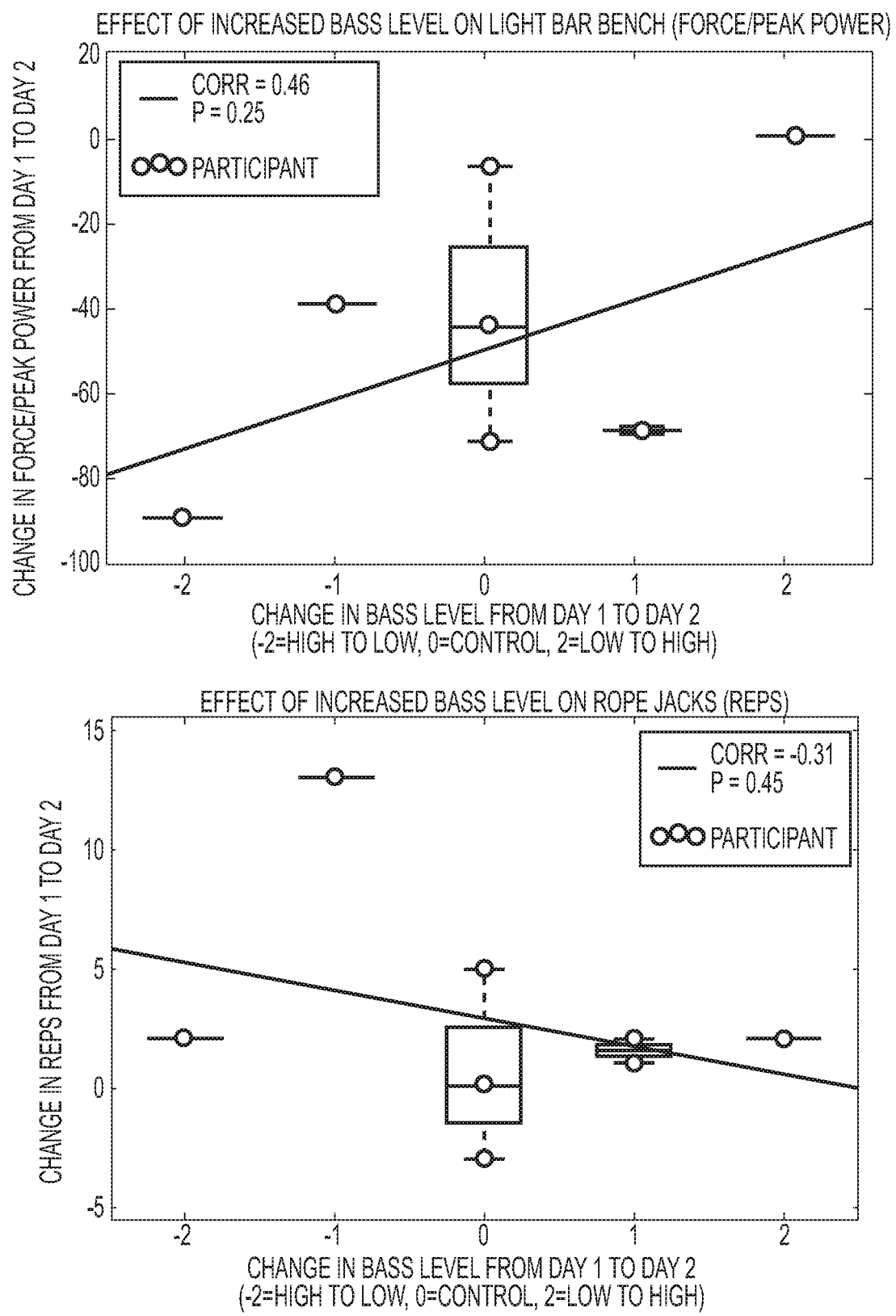
FIG. 7 shows the effect of increased bass level on specific exercises.

An increase in bass was associated with a decrease in maximum HRV in both univariate analysis (Corr=−0.70, p=0.05), as shown in FIG. 6, and multivariate regression controlling for physical characteristics, including age, height, and weight (Corr=−0.76, p<0.05). A similar pattern was observed for average HRV (univariate Corr=−0.67, p=0.07; multivariate Corr=−0.33, p=0.17). In multivariate regression, higher bass was also associated with higher average and maximum heart rate during recovery (Corr=0.44, p=0.16; Corr=0.46, p=0.13). Results for the relationship between bass and performance were inconclusive. Average completion times (minutes) for high bass athletes (13.00±0.00, day 1; 11.67±0.58, day 2) were lower than those for low and normal bass athletes (14.17±3.43, day 1; 13.20±2.17, day 2) on both days (p=0.44, day 1; p=0.20, day 2). Univariate analysis showed a positive correlation between bass and bar bench performance (Corr=0.46, p=0.25; FIG. 7), but this effect diminished when controlling for physical characteristics. Higher bass correlated with decreased performance in other exercises (e.g., rope jacks, Corr=−0.31, p=0.45), as shown in FIG. 7.

In the above example, listening to high bass music promotes increased effort during high intensity training by lowering heart rate variability and may inhibit recovery by elevating heart rate. Other music modulations can be programmed to, for example, increase relaxation. Modulation plans can be combined and/or delivered sequentially to achieve desired effects in the user.

What is claimed is:

1. A method for modifying performance of an activity by a human subject, the method performed by a system comprising at least one processor and at least one memory storing instructions which, when executed, cause the system to perform the method, the method comprising:
   acquiring biomedical metric data pertinent to the human subject from a wearable device worn by the human subject, the wearable device including at least one sensor for acquiring biomedical metric data;
   delivering the biomedical metric data to a stimulus selection engine of the at least one processor;
   determining a flow state value of the human subject using the biomedical metric data;
   comparing the determined flow state value to a desired flow state value using a proportional-integral-derivative (PID) control loop to determine a difference between the determined flow state value and the desired flow state value;

selecting an audio stimulus positively correlated to modify the biomedical metric data of the human subject, using the PID control loop, so as to decrease the difference between the determined flow state value and the desired flow state value, the audio stimulus selected from among plural stimuli with the stimulus selection engine of the at least one processor; and outputting the selected audio stimulus to the human subject via the wearable device.

2. The method of claim 1, wherein the selected audio stimulus is one or more sounds.

3. The method of claim 1, wherein:

selecting the audio stimulus from among the plural stimuli with the stimulus selection engine comprises selecting an attribute of a musical composition;

adjusting the audio stimulus based on the comparison and the determination that the determined flow state value is different from the desired flow state value comprising adjusting an attribute of the musical composition; and the attribute comprises at least one of genre, melody, harmony, rhythm, form, instrumentation, sonority, lyrics, vocal gender, tempo, timing signature, musical key, pitch, and frequency.

4. The method of claim 1, further comprising acquiring context data pertinent to the human subject.

5. The method of claim 4, wherein the context data and biomedical metric data include at least one of GPS location, velocity data, velocity rate of change information, real-time and/or forecast meteorological data, accelerometer data, gyroscope data, compass data, ambient light level, body temperature, altimeter data, humidity, blood oxygenation, pulse rate, heart rate variability, eye movement, jaw tension, head orientation, posture data, microgrimace or facial gesture data, auditory evoked potential data, P300 response data, EEG data, acoustic data, speech pattern recognition data, impedance, capnographic data, or ambient $O_2$ data.

6. The method of claim 4, wherein determining a flow state value of the human subject further comprises determining the flow state value of the human subject using the context data.

7. A system comprising at least one processor and at least one memory storing instructions which, when executed, cause the system to perform a method, the method comprising:

acquiring biomedical metric data pertinent to a subject from a wearable device worn by the subject, the wearable device including at least one sensor for acquiring biomedical metric data;

delivering the biomedical metric data to a stimulus selection engine of the at least one processor;

determining a flow state value of the subject using the biomedical metric data;

comparing the determined flow state value to a desired flow state value using a proportional-integral-derivative (PID) control loop to determine a difference between the determined flow state value and the desired flow state value;

selecting an audio stimulus positively correlated to modify the biomedical metric data of the subject, using the PID control loops, so as to decrease the difference between the determined flow state value and the desired flow state value, the audio stimulus selected from among plural stimuli with the stimulus selection engine of the at least one processor; and outputting the selected audio stimulus to the subject via the wearable device.

8. The system of claim 7, wherein the audio stimulus is one or more sounds.

9. The system of claim 7, wherein the audio stimulus comprises an attribute of a musical composition, the attribute comprising at least one of genre, melody, harmony, rhythm, form, instrumentation, sonority, lyrics, vocal gender, tempo, timing signature, musical key, pitch, and frequency.

10. The system of claim 7, further acquiring context data pertinent to the subject.

11. The system of claim 10, wherein the context data and biomedical metric data include at least one of GPS location, velocity data, velocity rate of change information, real-time and/or forecast meteorological data, accelerometer data, gyroscope data, compass data, ambient light level, body temperature, altimeter data, humidity, blood oxygenation, pulse rate, heart rate variability, eye movement, jaw tension, head orientation, posture data, microgrimace or facial gesture data, auditory evoked potential data, P300 response data, EEG data, acoustic data, speech pattern recognition data, impedance, capnographic data, or ambient $O_2$ data.

12. The system of claim 10, wherein determining a flow state value of the subject further comprises determining the flow state value of the subject using the context data.

* * * * *